United States Patent
Cai et al.

(10) Patent No.: US 9,056,949 B2
(45) Date of Patent: *Jun. 16, 2015

(54) MICHAEL ADDITION CURING CHEMISTRIES FOR SULFUR-CONTAINING POLYMER COMPOSITIONS EMPLOYING BIS(SULFONYL)ALKANOLS

(71) Applicant: PRC-DeSoto International, Inc., Sylmar, CA (US)

(72) Inventors: Juexiao Cai, Stevenson Ranch, CA (US); Lawrence G. Anderson, Allison Park, PA (US); Marfi Ito, Culver City, CA (US); Renhe Lin, Stevenson Ranch, CA (US)

(73) Assignee: PRC-DeSoto International, Inc., Sylmar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/923,941

(22) Filed: Jun. 21, 2013

(65) Prior Publication Data

US 2014/0378649 A1    Dec. 25, 2014

(51) Int. Cl.

| | |
|---|---|
| C08G 75/04 | (2006.01) |
| C08G 75/12 | (2006.01) |
| C07C 317/18 | (2006.01) |
| C08G 75/02 | (2006.01) |
| C09J 181/02 | (2006.01) |
| C08L 81/02 | (2006.01) |

(52) U.S. Cl.
CPC .............. *C08G 75/12* (2013.01); *C07C 317/18* (2013.01); *C08G 75/02* (2013.01); *C09J 181/02* (2013.01); *C08L 81/02* (2013.01)

(58) Field of Classification Search
USPC ............. 528/376, 375, 391; 568/21; 525/535; 428/407
See application file for complete search history.

(56) References Cited

U.S. PATENT DOCUMENTS

| | | | |
|---|---|---|---|
| 3,138,573 | A | 6/1964 | Le Faye et al. |
| 4,366,307 | A | 12/1982 | Singh et al. |
| 4,609,762 | A | 9/1986 | Morris et al. |
| 4,623,711 | A | 11/1986 | Morris et al. |
| 5,225,472 | A | 7/1993 | Cameron et al. |
| 5,270,364 | A | 12/1993 | Schwartz et al. |
| 5,284,888 | A | 2/1994 | Morgan |
| 6,123,179 | A | 9/2000 | Chen |
| 6,172,179 | B1 | 1/2001 | Zook et al. |
| 6,184,280 | B1 | 2/2001 | Shibuta |
| 6,525,168 | B2 | 2/2003 | Zook et al. |
| 7,671,145 | B2 | 3/2010 | Sawant et al. |
| 2006/0270796 | A1 | 11/2006 | Sawant et al. |
| 2010/0010133 | A1 | 1/2010 | Zook et al. |
| 2010/0041784 | A1* | 2/2010 | Loccufier et al. ............... 522/26 |
| 2010/0041839 | A1* | 2/2010 | Anderson et al. ............ 525/535 |
| 2011/0092639 | A1 | 4/2011 | Rao et al. |
| 2012/0238707 | A1 | 9/2012 | Hobbs et al. |
| 2012/0238708 | A1 | 9/2012 | Hobbs et al. |
| 2013/0345371 | A1 | 12/2013 | Anderson et al. |

FOREIGN PATENT DOCUMENTS

WO    WO 2013/192480 A2    12/2013

OTHER PUBLICATIONS

Mather et al., "Michael addition reactions in macromolecular design for emerging technologies," Progress in Polymer Science, 2006, vol. 31, p. 487-531 (45 pages).

* cited by examiner

*Primary Examiner* — Shane Fang
(74) *Attorney, Agent, or Firm* — William R. Lambert

(57) ABSTRACT

Michael addition curing chemistries in compositions comprising sulfur-containing polymers such as polythioethers and polysulfides are useful in aerospace sealant applications. Compositions employing Michael addition curing chemistries include sulfur-containing adducts comprising terminal Michael acceptor groups. In particular, the sulfur-containing adducts include terminal 1-(ethylenesulfonyl)-n-(vinylsulfonyl)alkanol groups.

26 Claims, No Drawings

MICHAEL ADDITION CURING CHEMISTRIES FOR SULFUR-CONTAINING POLYMER COMPOSITIONS EMPLOYING BIS(SULFONYL)ALKANOLS

FIELD

The present disclosure relates to the use of Michael addition curing chemistries in compositions comprising sulfur-containing polymers, such as polythioethers and polysulfides, useful in aerospace sealant applications. The disclosure also relates to sulfur-containing adducts having terminal Michael acceptor groups, and in particular terminal 1-(ethylenesulfonyl)-n-(vinylsulfonyl)alkanol terminal groups and compositions thereof.

BACKGROUND

Sealants useful in aerospace and other applications must satisfy demanding mechanical, chemical, and environmental requirements. The sealants can be applied to a variety of surfaces including metal surfaces, primer coatings, intermediate coatings, finished coatings, and aged coatings. In sealants such as those described in U.S. Pat. No. 6,123,179 an amine catalyst is used to provide a cured product. Such systems typically cure in over two hours and although the cured sealants exhibit acceptable fuel resistance and thermal resistance for many applications, a faster curing rate with improved performance is desirable.

SUMMARY

Michael addition curing chemistries are often used in acrylic-based polymer systems as disclosed in U.S. Pat. No. 3,138,573 and have been adapted for use in polysulfide compositions. Application of Michael addition curing chemistries to sulfur-containing polymers not only results in cured sealants with faster cure rates and enhanced performance including fuel resistance and thermal resistance, but also provides a sealant with improved physical properties, such as elongation, adhesion, and fuel resistance. The use of Michael addition curing chemistries in sulfur-containing polymer compositions is disclosed in U.S. application Ser. No. 13/529,237 filed on Jun. 21, 2012, which is incorporated by reference in its entirety. Sulfone-containing polythioethers having one or more sulfone groups incorporated into the backbone of the polythioether are disclosed in U.S. application Ser. No. 13/883,827 filed on Mar. 15, 2013, which is incorporated by reference in its entirety.

In a first aspect, sulfur-containing Michael acceptor adducts comprising at least two terminal 1-(ethylenesulfonyl)-n-(vinylsulfonyl)alkanol groups are provided.

In a second aspect, compositions are provided comprising a sulfur-containing polymer comprising at least two terminal groups reactive with Michael acceptor groups; and a bis(vinylsulfonyl)alkanol.

DETAILED DESCRIPTION

Definitions

For purposes of the following description, it is to be understood that embodiments provided by the present disclosure may assume various alternative variations and step sequences, except where expressly specified to the contrary. Moreover, other than in the examples, or where otherwise indicated, all numbers expressing, for example, quantities of ingredients used in the specification and claims are to be understood as being modified in all instances by the term "about." Accordingly, unless indicated to the contrary, the numerical parameters set forth in the following specification and attached claims are approximations that may vary depending upon the desired properties to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

Also, it should be understood that any numerical range recited herein is intended to include all sub-ranges encompassed therein. For example, a range of "1 to 10" is intended to include all sub-ranges between (and including) the recited minimum value of about 1 and the recited maximum value of about 10, that is, having a minimum value equal to or greater than about 1 and a maximum value of equal to or less than about 10. Also, in this application, the use of "or" means "and/or" unless specifically stated otherwise, even though "and/or" may be explicitly used in certain instances.

A dash ("-") that is not between two letters or symbols is used to indicate a point of bonding for a substituent or between two atoms. For example, —$CONH_2$ is bonded to another chemical moiety through the carbon atom.

"Alkanediyl" refers to a diradical of a saturated, branched or straight-chain, acyclic hydrocarbon group, having, for example, from 1 to 18 carbon atoms ($C_{1-18}$), from 1 to 14 carbon atoms ($C_{1-14}$), from 1 to 6 carbon atoms ($C_{1-6}$), from 1 to 4 carbon atoms ($C_{1-4}$), or from 1 to 3 hydrocarbon atoms ($C_{1-3}$). It will be appreciated that a branched alkanediyl has a minimum of three carbon atoms. In certain embodiments, the alkanediyl is $C_{2-14}$ alkanediyl, $C_{2-10}$ alkanediyl, $C_{2-8}$ alkanediyl, $C_{2-6}$ alkanediyl, $C_{2-4}$ alkanediyl, and in certain embodiments, $C_{2-3}$ alkanediyl. Examples of alkanediyl groups include methane-diyl (—$CH_2$—), ethane-1,2-diyl (—$CH_2CH_2$—), propane-1,3-diyl and iso-propane-1,2-diyl (e.g., —$CH_2CH_2CH_2$— and —$CH_3(CH_3)CH_2$—), butane-1,4-diyl (—$CH_2CH_2CH_2CH_2$—), pentane-1,5-diyl (—$CH_2CH_2CH_2CH_2CH_2$—), hexane-1,6-diyl (—$CH_2CH_2CH_2CH_2CH_2CH_2$—), heptane-1,7-diyl, octane-1,8-diyl, nonane-1,9-diyl, decane-1,10-diyl, dodecane-1,12-diyl, and the like.

"Alkanecycloalkane" refers to a saturated hydrocarbon group having one or more cycloalkyl and/or cycloalkanediyl groups and one or more alkyl and/or alkanediyl groups, where cycloalkyl, cycloalkanediyl, alkyl, and alkanediyl are defined herein. In certain embodiments, each cycloalkyl and/or cycloalkanediyl group(s) is $C_{3-6}$, $C_{5-6}$, and in certain embodiments, cyclohexyl or cyclohexanediyl. In certain embodiments, each alkyl and/or alkanediyl group(s) is $C_{1-6}$, $C_{1-4}$, $C_{1-3}$, and in certain embodiments, methyl, methanediyl, ethyl, or ethane-1,2-diyl. In certain embodiments, the alkanecycloalkane group is $C_{4-18}$ alkanecycloalkane, $C_{4-16}$ alkanecycloalkane, $C_{4-12}$ alkanecycloalkane, $C_{4-8}$ alkanecycloalkane, $C_{6-12}$ alkanecycloalkane, $C_{6-10}$ alkanecycloalkane, and in certain embodiments, $C_{6-9}$ alkanecycloalkane. Examples of alkanecycloalkane groups include 1,1,3,3-tetramethylcyclohexane and cyclohexylmethane.

"Alkanecycloalkanediyl" refers to a diradical of an alkanecycloalkane group. In certain embodiments, the alkanecycloalkanediyl group is $C_{4-18}$ alkanecycloalkanediyl, $C_{4-16}$ alkanecycloalkanediyl, $C_{4-12}$ alkanecycloalkanediyl, $C_{4-8}$ alkanecycloalkanediyl, $C_{6-12}$ alkanecycloalkanediyl, $C_{6-10}$ alkanecycloalkanediyl, and in certain embodiments, $C_{6-9}$ alkanecycloalkanediyl. Examples of alkanecycloalkanediyl groups include 1,1,3,3-tetramethylcyclohexane-1,5-diyl and cyclohexylmethane-4,4'-diyl.

"Alkanearene" refers to a hydrocarbon group having one or more aryl and/or arenediyl groups and one or more alkyl and/or alkanediyl groups, where aryl, arenediyl, alkyl, and alkanediyl are defined herein. In certain embodiments, each aryl and/or arenediyl group(s) is $C_{6-12}$, $C_{6-10}$, and in certain embodiments, phenyl or benzenediyl. In certain embodiments, each alkyl and/or alkanediyl group(s) is $C_{1-6}$, $C_{1-4}$, $C_{1-3}$, and in certain embodiments, methyl, methanediyl, ethyl, or ethane-1,2-diyl. In certain embodiments, the alkanearene group is $C_{4-18}$ alkanearene, $C_{4-16}$ alkanearene, $C_{4-12}$ alkanearene, $C_{4-8}$ alkanearene, $C_{6-12}$ alkanearene, $C_{6-10}$ alkanearene, and in certain embodiments, $C_{6-9}$ alkanearene. Examples of alkanearene groups include diphenyl methane.

"Alkanearenediyl" refers to a diradical of an alkanearene group. In certain embodiments, the alkanearenediyl group is $C_{4-18}$ alkanearenediyl, $C_{4-16}$ alkanearenediyl, $C_{4-12}$ alkanearenediyl, $C_{4-8}$ alkanearenediyl, $C_{6-12}$ alkanearenediyl, $C_{6-10}$ alkanearenediyl, and in certain embodiments, $C_{6-9}$ alkanearenediyl. Examples of alkanearenediyl groups include diphenyl methane-4,4'-diyl.

"Alkenyl" group refers to a group having the structure $—RC=C(R)_2$ where the alkenyl group is a terminal group and is bonded to a larger molecule. In such embodiments, each R may be selected from, for example, hydrogen and $C_{1-3}$ alkyl. In certain embodiments, each R is hydrogen and an alkenyl group has the structure $—CH=CH_2$.

"Alkoxy" refers to a OR group where R is alkyl as defined herein. Examples of alkoxy groups include methoxy, ethoxy, n-propoxy, isopropoxy, and n-butoxy. In certain embodiments, the alkoxy group is $C_{1-8}$ alkoxy, $C_{1-6}$ alkoxy, $C_{1-4}$ alkoxy, and in certain embodiments, $C_{1-3}$ alkoxy.

"Alkyl" refers to a monoradical of a saturated, branched or straight-chain, acyclic hydrocarbon group having, for example, from 1 to 20 carbon atoms, from 1 to 10 carbon atoms, from 1 to 6 carbon atoms, from 1 to 4 carbon atoms, or from 1 to 3 carbon atoms. It will be appreciated that a branched alkyl has a minimum of three carbon atoms. In certain embodiments, the alkyl group is $C_{1-6}$ alkyl, $C_{1-4}$ alkyl, and in certain embodiments, $C_{1-3}$ alkyl. Examples of alkyl groups include methyl, ethyl, n-propyl, iso-propyl, n-butyl, iso-butyl, tert-butyl, n-hexyl, n-decyl, tetradecyl, and the like. In certain embodiments, the alkyl group is $C_{1-6}$ alkyl, $C_{1-4}$ alkyl, and in certain embodiments, $C_{1-3}$ alkyl. It will be appreciated that a branched alkyl has at least three carbon atoms.

"Arenediyl" refers to diradical monocyclic or polycyclic aromatic group. Examples of arenediyl groups include benzene-diyl and naphthalene-diyl. In certain embodiments, the arenediyl group is $C_{6-12}$ arenediyl, $C_{6-10}$ arenediyl, $C_{6-9}$ arenediyl, and in certain embodiments, benzene-diyl.

A "bis(sulfonyl)alkanol group" refers to a group having the general formula:

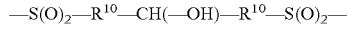

$$—S(O)_2—R^{10}—CH(—OH)—R^{10}—S(O)_2—$$

where each $R^{10}$ is independently selected from $C_{1-3}$ alkanediyl and substituted $C_{1-3}$ alkanediyl, where the one or more substituent groups is —OH. In certain embodiments, a bis(sulfonyl)alkanol group has the structure $—CH_2—CH_2—S(O)_2—R^{10}—CH(—OH)—R^{10}—S(O)_2—CH_2—CH_2—$ and in certain embodiments, the structure, $—R^9—S(O)_2—R^{10}—CH(—OH)—R^{10}—S(O)_2—R^9—$ where each $R^8$ comprises a terminal alkenyl group; and each $R^{10}$ is independently selected from $C_{1-3}$ alkanediyl and substituted $C_{1-3}$ alkanediyl, wherein the one or more substituent groups is —OH.

In certain embodiments, a "bis(sulfonyl)alkanol group" can be a monovalent bis(sulfonyl)alkanol group or a divalent bis(sulfonyl)alkanol group. In certain embodiments, a monovalent bis(sulfonyl)alkanol can be a terminal bis(sulfonyl)alkanol group such as a "1-(ethylenesulfonyl)-n-(vinylsulfonyl)alkanol group." A terminal bis(sulfonyl)alkanol group can be derived from the reaction of a bis(sulfonyl)alkanol and can have a terminal moiety with the general structure $—R^9—S(O)_2—R^{10}—CH(—OH)—R^{10}—S(O)_2—R^8$ where $R^9$ is a moiety derived from the reaction of a bis(sulfonyl)alkanol with a compound having a group reactive with the bis(sulfonyl)alkanol; each $R^{10}$ is independently selected from $C_{1-3}$ alkanediyl, and substituted $C_{1-3}$ alkanediyl, wherein the one or more substituent groups is —OH. In certain embodiments, $R^8$ is $—CH=CH_2$. In certain embodiments, a terminal bis(sulfonyl)alkanol group is a 1-(ethylenesulfonyl)-n-(vinylsulfonyl)alkanol group such as 1-(ethylenesulfonyl)-3-(vinylsulfonyl)propan-2-ol, i.e., $—CH_2—CH_2—S(O)_2—CH_2—CH(—OH)—CH_2—S(O)_2—CH=CH_2$. In certain embodiments, a terminal bis(sulfonyl)alkanol group has the structure $—CH_2—CH_2—S(O)_2—R^{15}—CH(—OH)—R^{15}—S(O)_2—CH=CH_2$.

In certain embodiments, a bis(sulfonyl)alkanol group can also be divalent such as when the group is incorporated into the backbone of a prepolymer such as the polythioethers disclosed in U.S. Application Publication No. 2014/0378650 filed concurrently with the present application. In certain embodiments, a divalent bis(sulfonyl)alkanol group can have the general structure $—R^9—S(O)_2—R^{15}—CH(—OH)—R^{15}—S(O)_2—R^9—$; in certain embodiments, $—CH_2—CH_2—S(O)_2—R^{15}—CH(—OH)—R^{15}—S(O)_2—CH_2—CH_2—$, in certain embodiments, $—R^9—S(O)_2—CH_2—CH(—OH)—CH_2—S(O)_2—R^9—$, and in certain embodiments, $—CH_2—CH_2—S(O)_2—CH_2—CH(—OH)—CH_2—S(O)_2—CH_2—CH_2—$, where $R^9$ and $R^{15}$ are as defined herein. In certain embodiments of a bis(sulfonyl)alkanol, each $R^8$ is an alkenyl group, each $R^9$ is an ethane-diyl group and/or each $R^{15}$ is methane-diyl.

A "bis(sulfonyl)alkanol" refers to a compound of the general formula $R^8—S(O)_2R^{15}—CH(—OH)—R^{15}—S(O)_2—R^8$ where each $R^8$ is a moiety having a terminal reactive group; and each $R^{10}$ is independently selected from $C_{1-3}$ alkanediyl and substituted $C_{1-3}$ alkanediyl, wherein the one or more substituent groups is —OH. In certain embodiments, each $R^8$ comprises a terminal group reactive with a thiol group such as, for example, an alkenyl group, an epoxy group, or a Michael acceptor group. In certain embodiments, a bis(sulfonyl)alkanol may be a bis(vinylsulfonyl)alkanol comprising terminal alkenyl groups. In certain embodiments a bis(sulfonyl)alkanol may be a bis(vinylsulfonyl)alkanol in which $R^8$ comprises a terminal alkenyl group, such as a compound having the formula $CH_2=CH—S(O)_2—R^{15}—CH(—OH)—R^{15}—S(O)_2—CH=CH_2$. In certain embodiments, a bis(vinylsulfonyl)alkanol is 1,3-bis(vinylsulfonyl)-2-propanol. In certain embodiments, a bis(sulfonyl)alkanol can be prepared by reacting a bis(vinylsulfonyl)alkanol with a compound having a reactive terminal functional group and a terminal group reactive with the terminal alkenyl groups of the bis(vinylsulfonyl)alkanol such as a thiol group or an epoxy group. In such embodiments, the bis(sulfonyl)alkanol can have the structure $R^{8'}—CH_2—CH_2—S(O)_2—R^{15}—CH(—OH)—R^{15}—S(O)_2—CH_2—CH_2—R^{8'}$ where each $R^8$ is a moiety derived from the reaction of the compound with the terminal alkenyl groups of the bis(vinylsulfonyl)alkanol.

A "bis(sulfonyl)alkanol-containing" polymer, prepolymer, or adduct refers to polymer, prepolymer, or adduct in which one or more divalent bis(sulfonyl)alkanol groups are incorporated into the backbone of the polymer, prepolymer, or adduct.

A divalent bis(sulfonyl)alkanol group can be incorporated in a prepolymer by reacting, for example, in a suitable ratio, a polythiol monomer or prepolymer of Formula A with a bis(sulfonyl)alkanol of Formula B:

$$R(-SH)_w \quad (A)$$

$$R^8-S(O)_2-R^{10}-CH(-OH)-R^{10}-S(O)_2-R^8 \quad (B)$$

where R is an organic moiety, w is an integer of at least 2 and each $R^8$ comprises a terminal group that is reactive with a thiol group such as, for example, an alkylene group, and epoxy group, or a group comprising a saturated carbon bearing a leaving group that are well suited for nucleophilic substitution such as, for example, —Cl, —Br, —I, —OSO$_2$CH$_3$ (mesylate), —OSO$_2$—C$_6$H$_4$—CH$_3$ (tosylate), etc. In certain embodiments, a bis(sulfonyl)alkanol of Formula B may be a bis(vinylsulfonyl)alkanol having the formula:

$$CH_2=CH-S(O)_2-R^{10}-CH(-OH)-R^{10}-S(O)_2-CH=CH_2$$

where each $R^{10}$ is independently selected from $C_{1-3}$ alkanediyl and substituted $C_{1-3}$ alkanediyl, wherein the one or more substituent groups is —OH. In certain embodiments, a bis(sulfonyl)alkanol may be 1,3-bis(vinylsulfonyl)-2-propanol. Alternatively, a bis(sulfonyl)alkanol group can be incorporated into a prepolymer backbone by reacting, in a suitable ratio, a thiol-capped bis(sulfonyl)alkanol of Formula C with a reactant of Formula D:

$$HS-R-S(O)_2-R^{10}-CH(-OH)-R^{10}-S(O)_2-R-SH \quad (C)$$

$$R''-R-R'' \quad (D)$$

where each R is a divalent moiety, each $R^{10}$ is as defined herein, and each R'' comprises a terminal group that is reactive with a thiol group such as, for example, an alkenyl group, an epoxy group, or a group consisting of a saturated carbon bearing a leaving group that are well known for nucleophilic substitution such as, for example, —Cl, —Br, —I, —OSO$_2$CH$_3$ (mesylate), —OSO$_2$—C$_6$H$_4$—CH$_3$ (tosylate), etc.

By choosing the appropriate ratio of the reactants of Formula A and Formula B, or Formula C and Formula D, one or more bis(sulfonyl)alkanol groups can be incorporated into a prepolymer as either a chain segment, as part of a terminal bearing a reactive group, or both. For example, bis(vinylsulfonyl)alkanol can be used to introduce one or more 1,n-bis(ethylenesulfonyl)alkanol groups into the backbone of a prepolymer chain, one or more terminal 1-(ethylenesulfonyl)-n-(vinylsulfonyl)alkanol groups, or both.

In certain embodiments, bis(vinylsulfonyl)-2-propanol can be reacted with thiol-capped monomers/polymers to incorporate 1,3-bis(ethylenesulfonyl)-2-propanol groups into the polymer chain.

In certain embodiments, bis(vinylsulfonyl)-2-propanol can be reacted with thiol-capped monomers/polymers to provide 1-(ethylenesulfonyl)-3-(vinylsulfonyl)-2-propanol terminal groups, where the terminal alkenyl group is a well-recognized Michael acceptor.

A moiety derived from the reaction of a bis(sulfonyl)alkanol with a thiol group refers to the reaction product a thiol group and a moiety containing a terminal group reactive with the thiol group. Examples of terminal groups reactive with thiol groups include epoxy groups, alkenyl groups, and Michael acceptor groups. In certain embodiments, a moiety derived from the reaction of a bis(sulfonyl)alkanol with a thiol group has the structure: —CH$_2$—CH$_2$R—, —CH(—OH)—CH$_2$—R—, —CH$_2$—CH(—OH)—R—, or —CH$_2$—CH$_2$—SO$_2$—R—, where R refers to a covalent bond or an organic moiety bonded to a sulfonyl group.

A moiety derived from the reaction of a bis(sulfonyl)alkanol with a thiol group also refers to a moiety $R^9$, which is derived from the reaction of group $R^8$ with a thiol group, where $R^8$ comprises a terminal group reactive with a thiol group.

In certain embodiments, $R^8$ is derived from the reaction of a bis(sulfonyl)alkanol with a compound having a terminal group reactive with a thiol group and a group reactive with a bis(sulfonyl)alkanol. In certain embodiments $R^8$ is derived from the reaction of a bis(vinylsulfonyl)alkanol with a compound having a terminal group reactive with a thiol group and a group reactive with an ethylene group. In such embodiment, $R^9$ may have the structure: —CH$_2$—CH$_2$—R'—CH$_2$—CH$_2$—, —CH(—OH)—CH$_2$—R'—CH$_2$—CH$_2$—, —CH$_2$—CH(—OH)—R'—CH$_2$—CH$_2$—, or —CH$_2$—CH$_2$—SO$_2$—R'—CH$_2$—CH$_2$—, where R' is an organic moiety derived from the reaction of the compound used to cap the bis(ethylenesulfonyl)alkanol with a functional group such as an ethylene group, an epoxy group, or a Michael acceptor group.

In certain embodiments, $R^9$ is selected from $C_{2-10}$ alkanediyl, substituted $C_{2-10}$ alkanediyl, $C_{2-10}$ heteroalkanediyl, substituted $C_{2-10}$ heteroalkanediyl, $C_{4-14}$ alkanecycloalkanediyl, substituted $C_{4-14}$ alkanecycloalkanediyl, $C_{4-14}$ heteroalkanecycloalkanediyl, substituted $C_{4-14}$ heteroalkanecycloalkanediyl, $C_{4-14}$ alkanearenediyl, substituted $C_{4-14}$ alkanearenediyl, $C_{4-14}$ heteroalkanearenediyl, and substituted $C_{4-14}$ heteroalkanearenediyl. In certain embodiments, $R^9$ is ethane-diyl.

In certain embodiments, $R^8$ is selected from $C_{2-10}$ alkyl, substituted $C_{2-10}$ alkyl, $C_{2-10}$ heteroalkyl, substituted $C_{2-10}$ heteroalkyl, $C_{4-14}$ alkanecycloalkyl, substituted $C_{4-14}$ alkanecycloalkyl, $C_{4-14}$ heteroalkanecycloalkyl, substituted $C_{4-14}$ heteroalkanecycloalkyl, $C_{4-14}$ alkanearyl, substituted $C_{4-14}$ alkanearyl, $C_{4-14}$ heteroalkanearyl, and substituted $C_{4-14}$ heteroalkanearyl. In certain embodiments, $R^8$ is ethylene, i.e., —CH=CH$_2$.

"Cycloalkanediyl" refers to a diradical saturated monocyclic or polycyclic hydrocarbon group. In certain embodiments, the cycloalkanediyl group is $C_{3-12}$ cycloalkanediyl, $C_{3-8}$ cycloalkanediyl, $C_{3-6}$ cycloalkanediyl, and in certain embodiments, $C_{5-6}$ cycloalkanediyl. Examples of cycloalkanediyl groups include cyclohexane-1,4-diyl, cyclohexane-1,3-diyl, and cyclohexane-1,2-diyl.

"Cycloalkyl" refers to a saturated monocyclic or polycyclic hydrocarbon monoradical group. In certain embodiments, the cycloalkyl group is $C_{3-12}$ cycloalkyl, $C_{3-8}$ cycloalkyl, $C_{3-6}$ cycloalkyl, and in certain embodiments, $C_{5-6}$ cycloalkyl.

"Heteroalkanediyl" refers to an alkanediyl group in which one or more of the carbon atoms are replaced with a heteroatom, such as N, O, S, or P. In certain embodiments of heteroalkanediyl, the heteroatom is selected from N and O.

"Heterocycloalkanediyl" refers to a cycloalkanediyl group in which one or more of the carbon atoms are replaced with a heteroatom, such as N, O, S, or P. In certain embodiments of heterocycloalkanediyl, the heteroatom is selected from N and O.

"Heteroarenediyl" refers to an arenediyl group in which one or more of the carbon atoms are replaced with a heteroatom, such as N, O, S, or P. In certain embodiments of heteroarenediyl, the heteroatom is selected from N and O.

"Heterocycloalkanediyl" refers to a cycloalkanediyl group in which one or more of the carbon atoms are replaced with a heteroatom, such as N, O, S, or P. In certain embodiments of heterocycloalkanediyl, the heteroatom is selected from N and O.

A "Michael acceptor" refers to substituted alkenealkyne compounds in which at least one alkenealkyne group is directly attached to one or more electron-withdrawing group such as carbonyl (—CO), nitro (—NO$_2$), nitrile (—CN), alkoxycarbonyl (—COOR), phosphonate (—PO(OR)$_2$), trifluoromethyl (—CF$_3$), sulfonyl (—SO$_2$), trifluoromethanesulfonyl (—SO$_2$CF$_3$), p-toluenesulfonyl (—SO$_2$—C$_6$H$_4$—CH$_3$), etc. Types of compounds that function as Michael acceptors are vinyl ketones, quinones, nitroalkenes, acrylonitriles, acrylates, methacrylates, cyanoacrylates, acrylamides, maleimides, dialkyl vinylphosphonate, and vinylsulfones. Other examples of Michael acceptors are disclosed in Mather et al., Prog. Polym. Sci. 2006, 31, 487-531. Michael acceptor compounds having more than one Michael acceptor group are also well known. Examples include diacrylates such as ethylene glycol diacrylate and diethylene glycol diacrylate, dimethacrylates such as ethylene glycol methacrylate and diethylene glycol methacrylate, bismaleimides such as N,N'-(1,3-phenylene)dimaleimide and 1,1'-(methylenedi-4,1-phenylene)bismaleimide, vinylsulfones such as divinyl sulfone and 1,3-bis(vinylsulfonyl)-2-propanol, etc. In certain embodiments, a Michael acceptor group has the structure of Formula (14a) or Formula (14b):

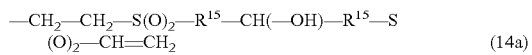    (14a)

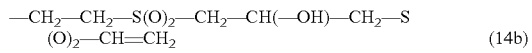    (14b)

where each R$^{15}$ is independently selected from C$_{1-3}$ alkanediyl and substituted C$_{1-3}$ alkanediyl, wherein the one or more substituent groups is —OH.

A "Michael acceptor compound" refers to a compound comprising at least one terminal Michael acceptor group. In certain embodiments, a Michael acceptor compound is divinyl sulfone, and a Michael acceptor group is vinylsulfonyl, i.e., —S(O)$_2$—CH=CH$_2$. In certain embodiments, a Michael acceptor compound is a bis(vinylsulfonyl)alkanol, and a Michael acceptor group is 1-(ethylenesulfonyl)-n-(vinylsulfonyl)alkanol, i.e., —CH$_2$—CH$_2$—S(O)$_2$—R$^{10}$—CH(—OH)—R$^{10}$—S(O)$_2$—CH=CH$_2$, and in certain embodiments, 1-(ethylenesulfonyl)-3-(vinylsulfonyl)propan-2-ol (—CH$_2$—CH$_2$—S(O)$_2$—CH$_2$—CH(—OH)—CH$_2$—S(O)$_2$—CH=CH$_2$).

A "polyalkoxysilyl group" refers to a group having the formula:

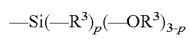

where p is selected from 0, 1, and 2; and each R$^3$ is independently selected from C$_{1-4}$ alkyl. In certain embodiments of a polyalkoxysilyl group, p is 0, p is 1, and in certain embodiments, p is 2. In certain embodiments of a polyalkoxysilyl group, each R$^3$ is independently selected from ethyl and methyl. In certain embodiments of a polyalkoxysilyl group, each R$^3$ is ethyl, and in certain embodiments, each R$^3$ is methyl. In certain embodiments of a polyalkoxysilyl group, the group is selected from —Si(—OCH$_2$CH$_3$)$_3$, —Si(—OCH$_3$)$_3$, —Si(—CH$_3$)(—OCH$_3$)$_2$, —Si(—CH$_3$)$_2$(—OCH$_3$), —Si(—CH$_3$)(—OCH$_2$CH$_3$)$_2$, —Si(—CH$_3$)$_2$(—OCH$_2$CH$_3$), —Si(—CH$_2$CH$_3$)(—OCH$_3$), and —Si(—CH$_2$CH$_3$)$_2$(—OCH$_3$).

As used herein, "polymer" refers to oligomers, homopolymers, and copolymers. Unless stated otherwise, molecular weights are number average molecular weights for polymeric materials indicated as "Mn" as determined, for example, by gel permeation chromatography using a polystyrene standard in an art-recognized manner.

"Substituted" refers to a group in which one or more hydrogen atoms are each independently replaced with the same or different substituent(s). In certain embodiments, the substituent is selected from halogen, —S(O)$_2$OH, —S(O)$_2$, —SH, —SR where R is C$_{1-6}$ alkyl, —COOH, —NO$_2$, —NR$_2$ where each R is independently selected from hydrogen and C$_{1-3}$ alkyl, —CN, =O, C$_{1-6}$ alkyl, —CF$_3$, —OH, phenyl, C$_{2-6}$ heteroalkyl, C$_{5-6}$ heteroaryl, C$_{1-6}$ alkoxy, and —COR where R is C$_{1-6}$ alkyl. In certain embodiments, the substituent is chosen from —OH, —NH$_2$, and C$_{1-3}$ alkyl. In certain embodiments, the substituent is chosen from —OH and C$_{1-3}$ alkyl, and in certain embodiments the one or more substituent group is —OH.

Reference is now made to certain embodiments of sulfur-containing adducts having terminal bis(sulfonyl)alkanol groups, polymers, compositions, and methods. The disclosed embodiments are not intended to be limiting of the claims. To the contrary, the claims are intended to cover all alternatives, modifications, and equivalents.

Sulfur-Containing Michael Acceptor Adducts

Sulfur-containing Michael acceptor adducts provided by the present disclosure comprise at least two terminal 1-(ethylenesulfonyl)-n-(vinylsulfonyl)alkanol groups. Sulfur-containing polymers useful herein include, for example, polythioethers, polysulfides, and combinations thereof. Examples of suitable polythioethers are disclosed in U.S. Pat. No. 6,123,179. Examples of suitable polysulfides are disclosed in U.S. Pat. No. 4,623,711. In certain embodiments, a sulfur-containing Michael acceptor adduct may be difunctional, and in certain embodiments, may have a functionality greater than 2 such as 3, 4, 5, or 6. A sulfur-containing adduct may comprise a mixture of sulfur-containing Michael acceptor adducts having different functionalities characterized by an average functionality from 2.05 to 6, from 2.1 to 4, from 2.1 to 3, from 2.2 to 2.8, and in certain embodiments, from 2.4 to 2.6. Sulfur-containing adducts have at least two terminal Michael acceptor groups, and in certain embodiments have two terminal 1-(ethylenesulfonyl)-n-(vinylsulfonyl)alkanol groups, 3, 4, 5, or 6 terminal 1-(ethylenesulfonyl)-n-(vinylsulfonyl)alkanol groups. A sulfur-containing Michael acceptor adduct may comprise a combination of adducts having different numbers of terminal 1-(ethylenesulfonyl)-n-(vinylsulfonyl)alkanol groups characterized, for example, by an average 1-(ethylenesulfonyl)-n-(vinylsulfonyl)alkanol functionality from 2.05 to 6, from 2.1 to 4, from 2.1 to 3, from 2.2 to 2.8, and in certain embodiments, from 2.4 to 2.6.

In certain embodiments, a sulfur-containing Michael acceptor adduct comprises a polythioether Michael acceptor adduct characterized by a polythioether having at least two terminal 1-(ethylenesulfonyl)-n-(vinylsulfonyl)alkanol groups.

In certain embodiments, a sulfur-containing Michael acceptor adduct comprises a polythioether Michael acceptor adduct comprising:

(a) a backbone comprising the structure of Formula (1):

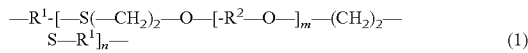

where (i) each $R^1$ is independently selected from a $C_{2-10}$ n-alkanediyl group, a $C_{3-6}$ branched alkanediyl group, a $C_{6-8}$ cycloalkanediyl group, a $C_{6-10}$ alkanecycloalkanediyl group, a heterocyclic group, a $-[(-CHR^3-)_p-X-]_q-(CHR^3)_r-$ group, wherein each $R^3$ is independently selected from hydrogen and methyl; (ii) each $R^2$ is independently selected from a $C_{2-10}$ n-alkanediyl group, a $C_{3-6}$ branched alkanediyl group, a $C_{6-8}$ cycloalkanediyl group, a $C_{6-14}$ alkanecycloalkanediyl group, a heterocyclic group, and a $-[(-CH_2-)_p-X-]_q-(CH_2)_r-$ group; (iii) each X is independently selected from O, S, and a $-NR^6-$ group, in which $R^6$ is selected from H and a methyl group; (iv) m ranges from 0 to 50; (v) n is an integer ranging from 1 to 60; (vi) p is an integer ranging from 2 to 6; (vii) q is an integer ranging from 1 to 5; and (viii) r is an integer ranging from 2 to 10; and (b) at least two terminal Michael acceptor groups.

In certain embodiments of a compound of Formula (1), $R^1$ is $-[-(CHR^3)_s-X-]_q-(CHR^3)_r-$ wherein each X is independently selected from $-O-$ and $-S-$. In certain embodiments wherein $R^1$ is $-[-(CHR^3)_s-X-]_q-(CHR^3)_r-$, each X is $-O-$ and in certain embodiments, each X is $-S-$.

In certain embodiments of a compound of Formula (1), $R^1$ is $-[-(CH_2)_s-X-]_q-(CH_2)_r-$ wherein each X is independently selected from $-O-$ and $-S-$. In certain embodiments wherein $R^1$ is $-[-(CH_2)_s-X-]_q-(CH_2)_r-$, each X is $-O-$ and in certain embodiments, each X is $-S-$.

In certain embodiments, $R^1$ in Formula (1) is $-[(-CH_2-)_p-X-]_q-(CH_2)_r-$, where p is 2, X is O, q is 2, r is 2, $R^2$ is ethanediyl, m is 2, and n is 9.

Michael acceptor groups are well known in the art. In certain embodiments, a Michael acceptor group comprises an activated alkene, such as an alkenyl group proximate to an electron-withdrawing group such as an enone, nitro, halo, nitrile, carbonyl, or nitro group. In certain embodiments, a Michael acceptor group is selected from a vinyl ketone, a vinyl sulfone, and a quinone. In certain embodiments, a Michael acceptor group comprises a bis(sulfonyl)alkanol group such as a 1-(ethylenesulfonyl)-n-(vinylsulfonyl)alkanol group, and in certain embodiments, a 1-(ethylenesulfonyl)-3-(vinylsulfonyl)propan-2-ol group. In certain embodiments, each of the Michael acceptor groups may be the same and in certain embodiments, at least some of the Michael acceptor groups are different.

In certain embodiments, a Michael acceptor group is derived from a vinyl sulfone and has the structure of Formula (11):

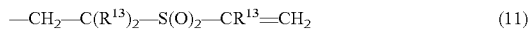

wherein each $R^{13}$ is independently selected from hydrogen and $C_{1-3}$ alkyl. In certain embodiments of Formula (11), each $R^{13}$ is hydrogen. In certain embodiments, Michael acceptor-terminated bis(sulfonyl)alkanol-containing polythioethers may be prepared, for example, by reacting a thiol-terminated bis(sulfonyl)alkanol-containing polythioether with a compound having a terminal Michael acceptor group and a group reactive with thiol groups such as a divinylsulfone, in the presence of an amine catalyst. Michael acceptor/polythioether chemistries and compounds are disclosed in U.S. application Ser. No. 13/529,237, filed on Jun. 21, 2012, which is incorporated by reference.

In certain embodiments, a Michael acceptor group is derived from a bis(sulfonyl)alkanol and has the structure of Formula (2a) or Formula (2b):

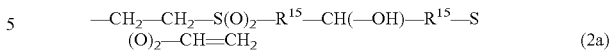

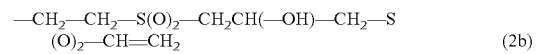

where each $R^{15}$ is independently selected from $C_{1-3}$ alkanediyl and substituted $C_{1-3}$ alkanediyl, where the one or more substituents is OH.

In certain embodiments where the sulfur-containing Michael acceptor adduct comprises a polythioether Michael acceptor adduct, the polythioether Michael acceptor adduct is selected from a polythioether adduct of Formula (3), a polythioether adduct of Formula (3a), and a combination thereof:

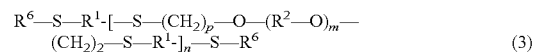

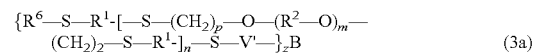

wherein:

each $R^1$ independently is selected from $C_{2-10}$ alkanediyl, $C_{6-8}$ cycloalkanediyl, $C_{6-10}$ alkanecycloalkanediyl, $C_{5-8}$ heterocycloalkanediyl, and $-[(-CHR^3-)_s-X-]_q-(-CHR^3-)_r-$, wherein:
s is an integer from 2 to 6;
q is an integer from 1 to 5;
r is an integer from 2 to 10;
each $R^3$ is independently selected from hydrogen and methyl; and
each X is independently selected from $-O-$, $-S-$, and $-NR-$, wherein R is selected from hydrogen and methyl;

each $R^2$ is independently selected from $C_{1-10}$ alkanediyl, $C_{6-8}$ cycloalkanediyl, $C_{6-14}$ alkanecycloalkanediyl, and $-[(-CHR^3-)_s-X-]_q-(-CHR_3-)_r-$, wherein s, q, r, $R^3$, and X are as defined for $R^1$;

m is an integer from 0 to 50;
n is an integer from 1 to 60;
p is an integer from 2 to 6;
B represents a core of a z-valent, vinyl-terminated polyfunctionalizing agent $B(-V)_z$, wherein:
z is an integer from 3 to 6; and
each V is a group comprising a terminal group reactive with thiol groups; and
each $-V'-$ is derived from the reaction of V with a thiol; and
each $R^6$ is independently a moiety comprising a terminal Michael acceptor group.

In certain embodiments of Formula (3) and in Formula (3a), $R^1$ is $-[(-CH_2-)_p-X-]_q-(CH_2)_r-$, where p is 2, X is $-O-$, q is 2, r is 2, $R^2$ is ethanediyl, m is 2, and n is 9.

In certain embodiments of Formula (3) and Formula (3a), $R^1$ is selected from $C_{2-6}$ alkanediyl and $-[-(CHR^3)_s-X-]_q-(CHR^3)_r-$.

In certain embodiments of Formula (3) and Formula (3a), $R^1$ is $-[-(CHR^3)_s-X-]_q-(CHR^3)_r-$, and in certain embodiments X is $-O-$ and in certain embodiments, X is $-S-$.

In certain embodiments of Formula (3) and Formula (3a), where $R^1$ is $-[-(CHR^3)_s-X-]_q-(CHR^3)_r-$, p is 2, r is 2, q is 1, and X is S; in certain embodiments, wherein p is 2, q is 2, r is 2, and X is $-O-$; and in certain embodiments, p is 2, r is 2, q is 1, and X is $-O-$.

In certain embodiments of Formula (3) and Formula (3a), where $R^1$ is $—[—(CHR^3)_s—X-]_q—(CHR^3)_r—$, each $R^3$ is hydrogen, and in certain embodiments, at least one $R^3$ is methyl.

In certain embodiment of adducts of Formula (3) and Formula (3a), each $R^1$ is the same, and in certain embodiments, at least one $R^1$ is different.

In certain embodiments, each —V comprises a terminal alkenyl group.

In certain embodiments of adducts of Formula (3) and Formula (3a), each $R^6$ is independently selected from a vinyl ketone, a vinyl sulfone, and a quinone. In certain embodiments, each of the Michael acceptor groups may be the same and in certain embodiments, at least some of the Michael acceptor groups are different.

In certain embodiments, each $R^6$ is independently a bis(sulfonyl)alkanol group.

In certain embodiments of adducts of Formula (3) and Formula (3a), each $R^6$ is independently derived from a bis(sulfonyl)alkanol and has the structure of Formula (2a) or Formula (2b):

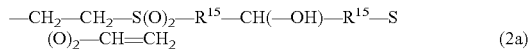

$$—CH_2—CH_2—S(O)_2—R^{15}—CH(—OH)—R^{15}—S(O)_2—CH=CH_2 \quad (2a)$$

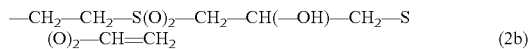

$$—CH_2—CH_2—S(O)_2—CH_2—CH(—OH)—CH_2—S(O)_2—CH=CH_2 \quad (2b)$$

where each $R^{15}$ is independently selected from $C_{1-3}$ alkanediyl and substituted $C_{1-3}$ alkanediyl, where the one or more substituents is —OH.

In certain embodiments, a sulfur-containing Michael acceptor adduct comprises a polysulfide adduct comprising at least two terminal Michael acceptor groups.

As used herein, the term polysulfide refers to a polymer that contains one or more disulfide linkages, i.e., —S—S— linkages, in the polymer backbone and/or in pendant positions on the polymer chain. In certain embodiments, the polysulfide polymer will have two or more sulfur-sulfur linkages. Suitable polysulfides are commercially available, for example, from Akzo Nobel and Toray Fine Chemicals under the names Thiokol-LP and Thioplast®. Thioplast® products are available in a wide range of molecular weights ranging, for example, from less than 1,100 to over 8,000, with molecular weight being the average molecular weight in grams per mole. In some cases, the polysulfide has a number average molecular weight of 1,000 to 4,000. The crosslink density of these products also varies, depending on the amount of crosslinking agent used. The —SH content, i.e., thiol or mercaptan content, of these products can also vary. The mercaptan content and molecular weight of the polysulfide can affect the cure speed of the polymer, with cure speed increasing with molecular weight.

In certain embodiments, a sulfur-containing Michael acceptor adduct comprises a polythioether Michael acceptor adduct comprising at least two terminal Michael acceptor groups, a polysulfide adduct comprising at least two terminal Michael acceptor groups, or a combination thereof.

In certain embodiments, sulfur-containing Michael acceptor adducts provided by the present disclosure comprise the reaction products of reactants comprising: (a) a sulfur-containing polymer; and (b) a compound having a terminal Michael acceptor group, such as a terminal bis(sulfonyl)alkanol group, and a group that is reactive with a terminal group of the sulfur-containing polymer.

In certain embodiments, the sulfur-containing polymer is selected from a polythioether, a polysulfide, and a combination thereof. In certain embodiments a sulfur-containing polymer comprises a polythioether, and in certain embodiments, a sulfur-containing polymer comprises a polysulfide. A sulfur-containing polymer may comprise a mixture of different polythioethers and/or polysulfides, and the polythioethers and/or polysulfides may have the same or different functionality. In certain embodiments, a sulfur-containing polymer has an average functionality from 2 to 6, from 2 to 4, from 2 to 3, and in certain embodiments, from 2.05 to 2.5. For example, a sulfur-containing polymer can be selected from a difunctional sulfur-containing polymer, a trifunctional sulfur-containing polymer, and a combination thereof.

In certain embodiments, a sulfur-containing polymer is terminated with a group that is reactive with the terminal reactive group of the compound having a terminal Michael acceptor group. In certain embodiments, the compound having a terminal Michael acceptor group has two Michael acceptor groups, and the terminal groups of the sulfur-containing polymer are reactive with Michael acceptor groups. A sulfur-containing polymer may comprise terminal thiol groups, terminal alkenyl groups, terminal amine groups, terminal isocyanate groups, or terminal epoxy groups.

In certain embodiments, a sulfur-containing polymer is thiol-terminated. Examples of thiol-functional polythioethers are disclosed, for example in U.S. Pat. No. 6,172,179. In certain embodiments, a thiol-functional polythioether comprises Permapol® P3.1E, available from PRC-DeSoto International Inc., Sylmar, Calif.

In certain embodiments, a sulfur-containing polymer comprises a polythioether comprising:

(a) a backbone comprising the structure of Formula (1):

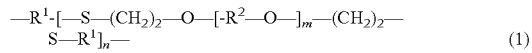

$$—R^1-[—S—(CH_2)_2—O—[-R^2—O—]_m—(CH_2)_2—S—R^1]_n— \quad (1)$$

wherein:
(i) each $R^1$ is independently selected from a $C_{2-10}$ n-alkanediyl group, a $C_{3-6}$ branched alkanediyl group, a $C_{6-8}$ cycloalkanediyl group, a $C_{6-10}$ alkanecycloalkanediyl group, a heterocyclic group, a $-[(—CHR^3-)_p—X-]_q—(CHR^3)_r—$ group, wherein each $R^3$ is selected from hydrogen and methyl;
(ii) each $R^2$ is independently selected from a $C_{2-10}$ n-alkanediyl group, a $C_{3-6}$ branched alkanediyl group, a $C_{6-8}$ cycloalkanediyl group, a $C_{6-14}$ alkanecycloalkanediyl group, a heterocyclic group, and a $-[(—CH_2-)_p—X-]_q—(CH_2)_r—$ group;
(iii) each X is independently selected from O, S, and a $—NR^6—$ group, in which $R^6$ is selected from H and a methyl group;
(iv) m ranges from 0 to 50;
(v) n is an integer ranging from 1 to 60;
(vi) p is an integer ranging from 2 to 6;
(vii) q is an integer ranging from 1 to 5; and
(viii) r is an integer ranging from 2 to 10.

In certain embodiments, a sulfur-containing polymer comprises a thiol-terminated polythioether selected from a thiol-terminated polythioether of Formula (4), a thiol-terminated polythioether of Formula (4a), and a combination thereof:

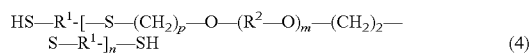

$$HS—R^1-[—S—(CH_2)_p—O—(R^2—O)_m—(CH_2)_2—S—R^1-]_n—SH \quad (4)$$

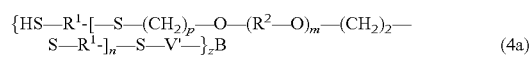

$$\{HS—R^1-[—S—(CH_2)_p—O—(R^2—O)_m—(CH_2)_2—S—R^1-]_n—S—V'—\}_zB \quad (4a)$$

wherein:
each $R^1$ independently is selected from $C_{2-10}$ alkanediyl, $C_{6-8}$ cycloalkanediyl, $C_{6-14}$ alkanecycloalkanediyl, $C_{5-8}$ heterocycloalkanediyl, and $-[(—CHR^3-)_s—X-]_q-(—CHR^3-)_r—$, wherein:

s is an integer from 2 to 6;
q is an integer from 1 to 5;
r is an integer from 2 to 10;
each $R^3$ is independently selected from hydrogen and methyl; and
each X is independently selected from —O—, —S—, and —NR, wherein R is selected from hydrogen and methyl;
each $R^2$ is independently selected from $C_{1-10}$ alkanediyl, $C_{6-8}$ cycloalkanediyl, $C_{6-14}$ alkanecycloalkanediyl, and -[(—$CHR^3$-)$_s$—X-]$_q$-(—$CHR^3$-)$_r$—, wherein s, q, r, $R^3$, and X are as defined as for $R^1$;
m is an integer from 0 to 50;
n is an integer from 1 to 60;
p is an integer from 2 to 6;
B represents a core of a z-valent, vinyl-terminated polyfunctionalizing agent B(—V)$_z$, wherein:
z is an integer from 3 to 6; and
each V is a group comprising a terminal group reactive with thiol groups; and
each —V'— is derived from the reaction of V with a thiol.

In certain embodiments, Formula (4) and in Formula (4a), $R^1$ is -[(—$CH_2$-)$_p$—X—]$_q$—($CH_2$)$_r$—, where p is 2, X is —O—, q is 2, r is 2, $R^2$ is ethanediyl, m is 2, and n is 9.

In certain embodiments of Formula (4) and Formula (4a), $R^1$ is selected from $C_{2-6}$ alkanediyl and -[—($CHR^3$)$_s$—X-]$_q$—($CHR^3$)$_r$—.

In certain embodiments of Formula (4) and Formula (4a), -[—($CHR^3$)$_s$—X-]$_q$—($CHR^3$)$_r$—, and in certain embodiments X is —O— and in certain embodiments, X is —S—.

In certain embodiments of Formula (4) and Formula (4a), where $R^1$ is —[—($CHR^3$)$_s$—X-]$_q$—($CHR^3$)$_r$—, p is 2, r is 2, q is 1, and X is —S—; in certain embodiments, wherein p is 2, q is 2, r is 2, and X is —O—; and in certain embodiments, p is 2, r is 2, q is 1, and X is —O—.

In certain embodiments of Formula (4) and Formula (4a), where $R^1$ is —[—($CHR^3$)$_s$—X-]$_q$—($CHR^3$)$_r$—, each $R^3$ is hydrogen, and in certain embodiments, at least one $R^3$ is methyl.

In certain embodiments of Formula (4) and Formula (4a), each $R^1$ is the same, and in certain embodiments, at least one $R^1$ is different.

Various methods can be used to prepare such polythioethers. Examples of suitable thiol-functional polythioethers, and methods for their production, are described in U.S. Pat. No. 6,172,179 at col. 2, line 29 to col. 4, line 22; col. 6, line 39 to col. 10, line 50; and col. 11, lines 65 to col. 12, line 22, the cited portions of which are incorporated herein by reference. Such thiol-functional polythioethers may be difunctional, that is, linear polymers having two thiol terminal groups, or polyfunctional, that is, branched polymers have three or more thiol terminal groups. Suitable thiol-functional polythioethers are commercially available, for example, as Permapol® P3.1E, from PRC-DeSoto International Inc., Sylmar, Calif.

In certain embodiments, a sulfur-containing polymer comprises a polythioether in which a bis(sulfonyl)alkanol is incorporated into the polymer backbone. In certain embodiments, a sulfur-containing polymer comprises a polythioether having the backbone structure:

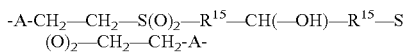

wherein:
each l e is independently selected from $C_{1-3}$ alkanediyl and substituted $C_{1-3}$ alkanediyl where the one or more substituent groups is —OH;

each A is independently a moiety having the structure:

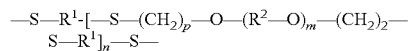

wherein:
each $R^1$ independently comprises $C_{2-10}$ alkanediyl, $C_{6-8}$ cycloalkanediyl, $C_{6-10}$ alkanecycloalkanediyl, $C_{5-8}$ heterocycloalkanediyl, or -[(—$CHR^3$-)$_s$—X-]$_q$—(—$CHR^3$-)$_r$—, wherein:
s is an integer from 2 to 6;
q is an integer from 1 to 5;
r is an integer from 2 to 10;
each $R^3$ independently comprises hydrogen or methyl; and
each X independently comprises —O—, —S—, and —$NR^5$—, wherein $R^5$ comprises hydrogen or methyl; and
each $R^2$ independently comprises $C_{1-10}$ alkanediyl, $C_{6-8}$ cycloalkanediyl, $C_{6-14}$ alkanecycloalkanediyl, or -[(—$CHR^3$-)$_s$—X-]$_q$-(—$CHR^3$-)$_r$—, wherein s, q, r, $R^3$, and X are as defined for $R^1$;
m is an integer from 0 to 50;
n is an integer from 1 to 60; and
p is an integer from 2 to 6.

These polythioethers, which contain a bis(sulfonyl)alkanol moiety within the backbone are disclosed in U.S. Application Publication No. 2014/0378650 filed concurrently with the present application, which is incorporated by reference in its entirety.

Suitable thiol-functional polythioethers may be produced by reacting a divinyl ether or mixtures of divinyl ethers with an excess of dithiol or a mixtures of dithiols. For example, dithiols suitable for use in preparing thiol-functional polythioethers include those having Formula (5), other dithiols disclosed herein, or combinations of any of the dithiols disclosed herein.

In certain embodiments, a dithiol has the structure of Formula (5):

$$HS—R^1—SH \qquad (5)$$

wherein:
$R^1$ is selected from $C_{2-6}$ alkanediyl, $C_{6-8}$ cycloalkanediyl, $C_{6-10}$ alkanecycloalkanediyl, $C_{5-8}$ heterocycloalkanediyl, and -[—($CHR^3$)$_s$—X-]$_q$—($CHR^3$)$_r$—;
wherein:
each $R^3$ is independently selected from hydrogen and methyl;
each X is independently selected from —O—, —S—, and —NR— wherein R is selected from hydrogen and methyl;
s is an integer from 2 to 6;
q is an integer from 1 to 5; and
r is an integer from 2 to 10.

In certain embodiments of a dithiol of Formula (5), $R^1$ is -[—($CHR^3$)$_s$—X-]$_q$—($CHR^3$)$_r$—.

In certain embodiments of a compound of Formula (5), X is selected from —O— and —S—, and thus -[—($CHR^3$)$_s$—X-]$_q$—($CHR^3$)$_r$— in Formula (5) is -[—($CHR^3$)$_p$—O—]$_q$-($CHR^3$)$_r$— or -[(—$CHR^3{}_2$-)$_p$—S—]$_q$-($CHR^3$)$_r$—. In certain embodiments, p and r are equal, such as where p and r are both two.

In certain embodiments of a dithiol of Formula (5), $R^1$ is selected from $C_{2-6}$ alkanediyl and -[—($CHR^3$)$_s$—X-]$_q$—($CHR^3$)$_r$—.

In certain embodiments, $R^1$ is -[—($CHR^3$)$_s$—X-]$_q$—($CHR^3$)$_r$—, and in certain embodiments X is —O—, and in certain embodiments, X is —S—.

In certain embodiments where $R^1$ is -[—(CHR$^3$)$_s$—X-]$_q$—(CHR$^3$)$_r$—, p is 2, r is 2, q is 1, and X is —S—; in certain embodiments, wherein p is 2, q is 2, r is 2, and X is —O—; and in certain embodiments, p is 2, r is 2, q is 1, and X is —O—.

In certain embodiments where $R^1$ is -[—(CHR$^3$)$_s$—X-]$_q$—(CHR$^3$)$_r$—, each $R^3$ is hydrogen, and in certain embodiments, at least one $R^3$ is methyl.

Examples of suitable dithiols include, for example, 1,2-ethanedithiol, 1,2-propanedithiol, 1,3-propanedithiol, 1,3-butanedithiol, 1,4-butanedithiol, 2,3-butanedithiol, 1,3-pentanedithiol, 1,5-pentanedithiol, 1,6-hexanedithiol, 1,3-dimercapto-3-methylbutane, dipentenedimercaptan, ethylcyclohexyldithiol (ECHDT), dimercaptodiethylsulfide, methyl-substituted dimercaptodiethylsulfide, dimethyl-substituted dimercaptodiethylsulfide, dimercaptodioxaoctane, 1,5-dimercapto-3-oxapentane, and a combination of any of the foregoing. A polythiol may have one or more pendant groups selected from a lower (e.g., $C_{1-6}$) alkyl group, a lower alkoxy group, and a hydroxyl group. Suitable alkyl pendant groups include, for example, $C_{1-6}$ linear alkyl, $C_{3-6}$ branched alkyl, cyclopentyl, and cyclohexyl.

Other examples of suitable dithiols include dimercaptodiethylsulfide (DMDS) (in Formula (5), $R^1$ is -[(—CH$_2$-)$_p$—X-]$_q$—(CH$_2$)$_r$—, wherein p is 2, r is 2, q is 1, and X is —S—); dimercaptodioxaoctane (DMDO) (in Formula (5), $R^1$ is -[(—CH$_2$-)$_p$—X-]$_q$—(CH$_2$)$_r$—, wherein p is 2, q is 2, r is 2, and X is —O—); and 1,5-dimercapto-3-oxapentane (in Formula (5), $R^1$ is -[(—CH$_2$-)$_p$—X-]$_q$—(CH$_2$)$_r$—, wherein p is 2, r is 2, q is 1, and X is —O—). It is also possible to use dithiols that include both heteroatoms in the carbon backbone and pendant alkyl groups, such as methyl groups. Such compounds include, for example, methyl-substituted DMDS, such as HS—CH$_2$CH(CH$_3$)—S—CH$_2$CH$_2$—SH, HS—CH(CH$_3$)CH$_2$—S—CH$_2$CH$_2$—SH and dimethyl substituted DMDS, such as HS—CH$_2$CH(CH$_3$)—S—CHCH$_3$CH$_2$—SH and HS—CH(CH$_3$)CH$_2$—S—CH$_2$CH(CH$_3$)—SH.

Suitable divinyl ethers for preparing polythioethers and polythioether adducts include, for example, divinyl ethers of Formula (6):

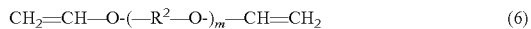

$$CH_2=CH-O-(-R^2-O-)_m-CH=CH_2 \quad (6)$$

where $R^2$ in Formula (6) is selected from a $C_{2-6}$ n-alkanediyl group, a $C_{3-6}$ branched alkanediyl group, a $C_{6-8}$ cycloalkanediyl group, a $C_{6-10}$ alkanecycloalkanediyl group, and -[(—CH$_2$-)$_p$—O-]$_q$-(—CH$_2$-)$_r$—, where p is an integer ranging from 2 to 6, q is an integer from 1 to 5, and r is an integer from 2 to 10. In certain embodiments of a divinyl ether of Formula (6), $R^2$ is a $C_{2-6}$ n-alkanediyl group, a $C_{3-6}$ branched alkanediyl group, a $C_{6-8}$ cycloalkanediyl group, a $C_{6-10}$ alkanecycloalkanediyl group, and in certain embodiments, -[(—CH$_2$-)$_p$—O-]$_q$-(—CH$_2$-)$_r$—.

Suitable divinyl ethers include, for example, compounds having at least one oxyalkanediyl group, such as from 1 to 4 oxyalkanediyl groups, i.e., compounds in which m in Formula (6) is an integer ranging from 1 to 4. In certain embodiments, m in Formula (6) is an integer ranging from 2 to 4. It is also possible to employ commercially available divinyl ether mixtures that are characterized by a non-integral average value for the number of oxyalkanediyl units per molecule. Thus, m in Formula (6) can also take on rational number values ranging from 0 to 10.0, such as from 1.0 to 10.0, from 1.0 to 4.0, or from 2.0 to 4.0.

Examples of suitable divinyl ethers include, for example, divinyl ether, ethylene glycol divinyl ether (EG-DVE) ($R^2$ in Formula (6) is ethanediyl and m is 1), butanediol divinyl ether (BD-DVE) ($R^2$ in Formula (6) is butanediyl and m is 1), hexanediol divinyl ether (HD-DVE) ($R^2$ in Formula (6) is hexanediyl and m is 1), diethylene glycol divinyl ether (DEG-DVE) ($R^2$ in Formula (4) is ethanediyl and m is 2), triethylene glycol divinyl ether ($R^2$ in Formula (14) is ethanediyl and m is 3), tetraethylene glycol divinyl ether ($R^2$ in Formula (6) is ethanediyl and m is 4), cyclohexanedimethanol divinyl ether, polytetrahydrofuryl divinyl ether; trivinyl ether monomers, such as trimethylolpropane trivinyl ether; tetrafunctional ether monomers, such as pentaerythritol tetravinyl ether; and combinations of two or more such polyvinyl ether monomers. A polyvinyl ether may have one or more pendant groups selected from alkyl groups, hydroxyl groups, alkoxy groups, and amine groups.

In certain embodiments, divinyl ethers in which $R^2$ in Formula (6) is $C_{3-6}$ branched alkanediyl may be prepared by reacting a polyhydroxy compound with acetylene. Examples of divinyl ethers of this type include compounds in which $R^2$ in Formula (6) is an alkyl-substituted methanediyl group such as CH(CH$_3$) (for example Pluriol® blends such as Pluriol®E-200 divinyl ether (BASF Corp., Parsippany, N.J.), for which $R^2$ in Formula (6) is ethanediyl and m is 3.8) or an alkyl-substituted ethanediyl (for example CH$_2$CH(CH$_3$)) such as DPE polymeric blends including DPE-2 and DPE-3 (International Specialty Products, Wayne, N.J.)).

Other useful divinyl ethers include compounds in which $R^2$ in Formula (6) is polytetrahydrofuryl (poly-THF) or polyoxyalkanediyl, such as those having an average of about 3 monomer units.

Two or more types of polyvinyl ether monomers of Formula (6) may be used. Thus, in certain embodiments, two dithiols of Formula (5) and one polyvinyl ether monomer of Formula (6), one dithiol of Formula (5) and two polyvinyl ether monomers of Formula (6), two dithiols of Formula (5) and two divinyl ether monomers of Formula (6), and more than two compounds of one or both Formula (5) and Formula (6), may be used to produce a variety of thiol-functional polythioethers.

In certain embodiments, a polyvinyl ether monomer comprises 20 to less than 50 mole percent of the reactants used to prepare a thiol-functional polythioether, and in certain embodiments, 30 to less than 50 mole percent.

In certain embodiments provided by the present disclosure, relative amounts of dithiols and divinyl ethers are selected to yield polythioethers having terminal thiol groups. Thus, a dithiol of Formula (5) or a mixture of at least two different dithiols of Formula (5), are reacted with of a divinyl ether of Formula (6) or a mixture of at least two different divinyl ethers of Formula (6) in relative amounts such that the molar ratio of thiol groups to vinyl groups is greater than 1:1, such as 1.1 to 2.0:1.0.

The reaction between compounds of dithiols and divinyl ethers may be catalyzed by a free radical catalyst. Suitable free radical catalysts include, for example, azo compounds, for example azobisnitriles such as azo(bis)isobutyronitrile (AIBN); organic peroxides such as benzoyl peroxide and t-butyl peroxide; and inorganic peroxides such as hydrogen peroxide. The catalyst may be a free-radical catalyst, an ionic catalyst, or ultraviolet radiation. In certain embodiments, the catalyst does not comprise acidic or basic compounds, and does not produce acidic or basic compounds upon decomposition. Examples of free-radical catalysts include azo-type catalyst, such as Vazo®-57 (Du Pont), Vazo®-64 (Du Pont), Vazo®-67 (Du Pont), V-70® (Wako Specialty Chemicals), and V-65B® (Wako Specialty Chemicals). Examples of other free-radical catalysts are alkyl peroxides, such as t-butyl peroxide. The reaction may also be effected by irradiation with ultraviolet light either with or without a cationic photoinitiating moiety.

Thiol-functional polythioethers provided by the present disclosure may be prepared by combining at least one compound of Formula (5) and at least one compound of Formula (6) followed by addition of an appropriate catalyst, and carrying out the reaction at a temperature from 30° C. to 120° C., such as 70° C. to 90° C., for a time from 2 to 24 hours, such as 2 to 6 hours.

As disclosed herein, thiol-terminated polythioethers may comprise a polyfunctional polythioether, i.e., may have an average functionality of greater than 2.0. Suitable polyfunctional thiol-terminated polythioethers include, for example, those having the structure of Formula (7):

$$B(\text{-}A\text{-}SH)_z \tag{7}$$

wherein: (i) A comprises, for example, a structure of Formula (1), (ii) B denotes a z-valent residue of a polyfunctionalizing agent; and (iii) z has an average value of greater than 2.0, and, in certain embodiments, a value between 2 and 3, a value between 2 and 4, a value between 3 and 6, and in certain embodiments, is an integer from 3 to 6.

Polyfunctionalizing agents suitable for use in preparing such polyfunctional thiol-functional polymers include trifunctionalizing agents, that is, compounds where z is 3. Suitable trifunctionalizing agents include, for example, triallyl cyanurate (TAC), 1,2,3-propanetrithiol, isocyanurate-containing trithiols, and combinations thereof, as disclosed in U.S. Publication No. 2010/0010133 at paragraphs [0102]-[0105], the cited portion of which is incorporated herein by reference. Other useful polyfunctionalizing agents include trimethylolpropane trivinyl ether, and the polythiols described in U.S. Pat. Nos. 4,366,307; 4,609,762; and 5,225,472. Mixtures of polyfunctionalizing agents may also be used.

As a result, thiol-functional polythioethers suitable for use in embodiments provided by the present disclosure may have a wide range of average functionality. For example, trifunctionalizing agents may afford average functionalities from 2.05 to 3.0, such as from 2.1 to 2.6. Wider ranges of average functionality may be achieved by using tetrafunctional or higher functionality polyfunctionalizing agents. Functionality may also be affected by factors such as stoichiometry, as will be understood by those skilled in the art.

Thiol-functional polythioethers having a functionality greater than 2.0 may be prepared in a manner similar to the difunctional thiol-functional polythioethers described in U.S. Publication No. 2010/0010133. In certain embodiments, polythioethers may be prepared by combining (i) one or more dithiols described herein, with (ii) one or more divinyl ethers described herein, and (iii) one or more polyfunctionalizing agents. The mixture may then be reacted, optionally in the presence of a suitable catalyst, to afford a thiol-functional polythioether having a functionality greater than 2.0.

Thus, in certain embodiments, a thiol-terminated polythioether comprises the reaction product of reactants comprising:

(a) a dithiol of Formula (5):

$$HS\text{---}R^1\text{---}SH \tag{5}$$

wherein:
R$^1$ is selected from C$_{2-6}$ alkanediyl, C$_{6-8}$ cycloalkanediyl, C$_{6-10}$ alkanecycloalkanediyl, C$_{5-8}$ heterocycloalkanediyl, and -[—(CHR$^3$)$_s$—X-]$_q$—(CHR$^3$)$_r$—;
wherein:
each R$^3$ is independently selected from hydrogen and methyl;
each X is independently selected from —O—, —S—, —NH—, and —NR— wherein R is selected from hydrogen and methyl;

s is an integer from 2 to 6;
q is an integer from 1 to 5; and
r is an integer from 2 to 10; and (b) a divinyl ether of Formula (6):

$$CH_2\!=\!CH\text{---}O\text{---}[\text{-}R^2\text{---}O\text{-}]_m\text{---}CH\!=\!CH_2 \tag{6}$$

wherein:
each R$^2$ is independently selected from C$_{1\text{-}10}$ alkanediyl, C$_{6\text{-}8}$ cycloalkanediyl, C$_{6\text{-}14}$ alkanecycloalkanediyl, and -[(—CHR$^3$-)$_s$—X-]$_q$-(—CHR$^3$-)$_r$—, wherein s, q, r, R$^3$, and X are as defined above;
m is an integer from 0 to 50;
n is an integer from 1 to 60; and
p is an integer from 2 to 6.

And, in certain embodiments, the reactants comprise (c) a polyfunctional compound such as a polyfunctional compound B(—V)$_z$, where B, —V, and z are as defined herein.

Thiol-terminated polythioethers provided by the present disclosure represent thiol-terminated polythioethers having a molecular weight distribution. In certain embodiments, useful thiol-terminated polythioethers can exhibit a number average molecular weight ranging from 500 Daltons to 20,000 Daltons, in certain embodiments, from 2,000 Daltons to 5,000 Daltons, and in certain embodiments, from 3,000 Daltons to 4,000 Daltons. In certain embodiments, useful thiol-terminated polythioethers exhibit a polydispersity (M$_w$/M$_n$; weight average molecular weight/number average molecular weight) ranging from 1 to 20, and in certain embodiments, from 1 to 5. The molecular weight distribution of thiol-terminated polythioethers may be characterized by gel permeation chromatography.

In certain embodiments, thiol-functional polythioethers provided by the present disclosure are essentially free, or free, of sulfone, ester and/or disulfide linkages. As used herein, "essentially free of sulfone, ester, and/or disulfide linkages" means that less than 2 mole percent of the linkages in the thiol-functional polymer are sulfone, ester, and/or disulfide linkages. As a result, in certain embodiments, the resulting thiol-functional polythioethers are also essentially free, or free, of sulfone, ester, and/or disulfide linkages.

To prepare a sulfur-containing Michael acceptor adduct, a sulfur-containing polymer such as those disclosed herein may be reacted with a compound having a Michael acceptor group and a group that is reactive with the terminal groups of the sulfur-containing polymer.

In certain embodiments a compound having a Michael acceptor group and a group that is reactive with the terminal groups of the sulfur-containing polymer may be a bis(sulfonyl)alkanol having the formula R—CH$_2$—CH$_2$—S(O)$_2$—R$^{15}$CH(—OH)—R$^{15}$—S(O)$_2$—CH=CH$_2$ where R is a moiety having a terminal group that is reactive with the terminal groups of the sulfur-containing polymer; and each R$^{15}$ is independently selected from C$_{1\text{-}3}$ alkanediyl, and substituted C$_{1\text{-}3}$ alkanediyl, wherein the one or more substituent groups is —OH. In certain embodiments, the bis(vinyl)alkanol is a bis(vinylsulfonyl)alkanol.

In certain embodiments, a Michael acceptor group is selected from a vinyl ketone, a vinyl sulfone, and a quinone, a. In certain embodiments, a Michael acceptor group is a vinyl ketone, and in certain embodiments, a vinyl sulfone such as derived from divinyl sulfone. In embodiments in which the compound having a Michael acceptor group is derived from divinyl sulfone, the sulfur-containing polymer may be thiol-terminated such as a thiol-terminated polythioether, a thiol-terminated polysulfide, or a combination thereof.

In certain embodiments, a Michael acceptor group is a bis(sulfonyl)alkanol such as a group derived from a bis(vinylsulfonyl) alkanol. In embodiments in which the compound having a Michael acceptor group is derived from bis(vinylsulfonyl)alkanol the sulfur-containing polymer may be thiol-terminated such as a thiol-terminated polythioether, a thiol-terminated polysulfide, or a combination thereof.

The reaction between a sulfur-containing polymer and a compound having a Michael acceptor group and a group that is reactive with a terminal group of the sulfur-containing polymer can be performed in the presence of an appropriate catalyst.

In certain embodiments, compositions provided by the present disclosure comprise a catalyst such as an amine catalyst. For example, in embodiments in which the sulfur-containing polymer is thiol-terminated and the compound is a difunctional Michael acceptor, the reaction may take place in the presence of an amine catalyst. Examples of suitable amine catalysts include, for example, triethylenediamine(1,4-diazabicyclo[2.2.2]octane, DABCO), dimethylcyclohexylamine (DMCHA), dimethylethanolamine (DMEA), bis-(2-dimethylaminoethyl)ether, N-ethylmorpholine, triethylamine, 1,8-diazabicyclo[5.4.0]undecene-7 (DBU), pentamethyldiethylenetriamine (PMDETA), benzyldimethylamine (BDMA), N,N,N'-trimethyl-N'-hydroxyethyl-bis(aminoethyl)ether, and N'-(3-(dimethylamino)propyl)-N,N-dimethyl-1,3-propanediamine.

Compositions

Michael addition chemistries may be employed in a variety of ways in conjunction with sulfur-containing polymers and sulfur-containing Michael acceptor adducts to provide curable compositions. For example, a curable composition provided by the present disclosure may comprise (a) a sulfur-containing polymer and a Michael acceptor curing agent; (b) a sulfur-containing Michael acceptor adduct and a curing agent comprising at least two terminal groups that are reactive with Michael acceptor groups; or (c) a sulfur-containing polymer and a curing agent comprising a combination of a monomeric Michael acceptors and a sulfur-containing Michael acceptor adduct.

Sulfur-Containing Polymer and Michael Acceptor Curing Agent

In certain embodiments, compositions provided by the present disclosure comprise a sulfur-containing polymer and a Michael acceptor curing agent. A sulfur-containing polymer may be a polythioether or combination of polythioethers having terminal groups reactive with the Michael acceptor curing agent; a polysulfide or combination of polysulfides having terminal groups reactive with the Michael acceptor curing agent; or a combination of any of the foregoing. In certain embodiments, a sulfur-containing polymer is thiol-terminated. In such embodiments, a Michael acceptor curing agent will be polyfunctional and have Michael acceptor groups reactive with the terminal groups of the sulfur-containing polymer.

In certain embodiments, a sulfur-containing polymer comprises a thiol-terminated polythioether, including any of the thiol-terminated polythioethers disclosed herein, such as a thiol-terminated polythioether of Formula (1). In certain embodiments, a sulfur-containing polymer comprises a thiol-terminated polythioether, such as a thiol-terminated polythioether of Formula (4), Formula (4a), or a combination thereof. In certain embodiments, a sulfur-containing polymer is selected from a difunctional sulfur-containing polymer, a trifunctional-containing polymer, and a combination of thereof.

In certain embodiments, a thiol-terminated polymer comprises a mixture of thiol-terminated sulfur-containing polymers having an average functionality from 2 to 3, and in certain embodiments, from 2.2 to 2.8. In certain embodiments, a thiol-terminated polythioether comprises Permapol® 3.1E, available from PRC-DeSoto International.

A polyfunctional Michael acceptor has at least two Michael acceptor groups. A polyfunctional Michael acceptor may have an average Michael acceptor functionality from 2 to 6, from 2 to 4, from 2 to 3, and in certain embodiments, from 2.05 to 2.5. In certain embodiments, a polyfunctional Michael acceptor is difunctional, such as, divinyl ketone and divinyl sulfone. A Michael acceptor having a functionality greater than two may be prepared by reacting a compound having a Michael acceptor group and a group reactive with terminal groups of a polyfunctionalizing agent such as those disclosed herein, using appropriate reaction conditions.

In certain embodiments, a Michael acceptor curing agent is a bis(vinylsulfonyl)alkanol such as 1,3-bis(vinylsulfonyl)-2-propanol.

In certain embodiments where a Michael acceptor is used as a curing agent, the molecular weight of the Michael acceptor curing agent is less than 600 Daltons, less than 400 Daltons, and in certain embodiments, less than 200 Daltons.

In certain embodiments, a Michael acceptor curing agent comprises from about 0.5 wt % to about 20 wt % of the composition, from about 1 wt % to about 10 wt %, from about 2 wt % to about 8 wt %, from about 2 wt % to about 6 wt %, and in certain embodiments, from about 3 wt % to about 5 wt %, where wt % is based on the total dry solids weight of the composition.

Sulfur-Containing Michael Acceptor Adduct and a Curing Agent

In certain embodiments, a composition comprises a sulfur-containing Michael acceptor adduct provided by the present disclosure and a sulfur-containing polymer curing agent.

In such compositions a sulfur-containing Michael acceptor adduct comprises any of those disclosed herein. In certain embodiments, a sulfur-containing Michael acceptor adduct comprises a polythioether Michael acceptor adduct, and in certain embodiments a polythioether Michael acceptor adduct has an average functionality from 2 to 3, from 2.2 to 2.8, and in certain embodiments, from 2.4 to 2.6. In certain embodiments, a sulfur-containing Michael acceptor adduct has an average functionality of 2.

In certain embodiments, a sulfur-containing Michael acceptor adduct comprises an adduct of Formula (3), Formula (3a), or a combination thereof, and the sulfur-containing polymer curing agent comprises a polythioether of Formula (4), Formula (4a), or a combination thereof. In certain embodiments, the sulfur-containing Michael acceptor adduct comprises the Michael acceptor adduct of Permapol® 3.1E. In certain embodiments, the sulfur-containing polymer curing agent comprises Permapol® 3.1E.

In certain embodiments, a sulfur-containing Michael acceptor adduct comprises an adduct of Formula (3), Formula (3a), or a combination thereof, and the sulfur-containing polymer curing agent comprises a polysulfide. In certain embodiments, the sulfur-containing Michael acceptor adduct comprises the Michael acceptor adduct of Permapol® 3.1E. In certain embodiments, the sulfur-containing polymer curing agent comprises a polysulfide selected from a Thiokol-LP® polysulfide, a Thioplast® polysulfide, and a combination thereof.

In such compositions the Michael acceptor groups of the adduct are reactive with the terminal groups of the sulfur-containing polymer. For example, the Michael acceptor groups may be activated alkenyl groups, e.g., Michael acceptor groups, and the sulfur-containing polymer comprises terminal thiol groups.

A sulfur-containing polymer used as a curing agent comprises at least two terminal groups reactive with Michael acceptor groups. A sulfur-containing polymer used as a curing agent in such compositions may comprise a polythioether including any of those disclosed herein, a polysulfide including any of those disclosed herein, or a combination thereof. The sulfur-containing polymer may have an average functionality of about 2 or any functionality from about 2 and about 6, such as from about 2 to about 4, or from about 2 to about 3.

In certain embodiments, the sulfur-containing polymer curing agent comprises a thiol-terminated polythioether such as, for example, Permapol® 3.1E. In certain embodiments, the sulfur-containing polymer comprises a thiol-terminated polysulfide such as, for example, a Thiokol-LP® polysulfide, a Thioplast® polysulfide, or a combination thereof.

In such embodiments, when used as a curing agent, a sulfur-containing polymer, comprises from about 20 wt % to about 90 wt % of the composition, from about 30 wt % to about 80 wt %, from about 40 wt % to about 60 wt %, and in certain embodiments, about 50 wt %, where wt % is based on the total dry weight of the composition.

In such embodiments, a sulfur-containing Michael acceptor adduct comprises from about 20 wt % to about 90 wt % of the composition, from about 30 wt % to about 80 wt %, from about 40 wt % to about 60 wt %, and in certain embodiments, about 50 wt %, where wt % is based on the total dry weight of the composition.

Compositions comprising a sulfur-containing Michael acceptor adduct and a sulfur-containing polymer curing agent may comprise a catalyst such as an amine catalyst including any of those disclosed herein.

In certain embodiments, a composition comprises a polythioether adduct and a curing agent. A polythioether adduct includes any of those disclosed herein, such as polythioether adducts of Formula (3), Formula (3a), and combinations thereof.

In certain embodiments of such compositions, the composition comprises a sulfur-containing Michael acceptor adduct provided by the present disclosure and a curing agent selected from a sulfur-containing polymer comprising at least two terminal groups reactive with Michael acceptor groups, a monomeric thiol, a polythiol, a polyamine, a blocked polyamine, and a combination of any of the foregoing. In certain embodiments, a curing agent comprises a sulfur-containing polymer comprising at least two terminal groups reactive with Michael acceptor groups such as a monomeric thiol, a polythiol, a polyamine, and in certain embodiments, a blocked polyamine. In certain embodiments of such compositions, a curing agent comprises a sulfur-containing polymer comprising at least two terminal groups reactive with Michael acceptor groups and a compound having at least two terminal groups reactive with Michael acceptor groups selected from a monomeric thiol, a polythiol, a polyamine, a blocked polyamine, and a combination of any of the foregoing.

In certain embodiments, a sulfur-containing polymer comprising at least two terminal groups reactive with Michael acceptor groups is selected from a polythioether polymer comprising at least two terminal groups reactive with Michael acceptor groups, a polysulfide polymer comprising at least two terminal groups reactive with Michael acceptor groups, and a combination thereof. In certain embodiments, the terminal groups reactive with Michael acceptor groups are thiol groups. In such embodiments, a thiol-terminated polythioether may be selected from a polythioether of Formula (4), a polythioether of Formula (4a), and a combination thereof. In certain embodiments, the sulfur-containing polymer curing agent comprises a thiol-terminated polysulfide such as, for example, Thiokol-LP® and Thioplast® polysulfide polymers.

In certain compositions, the curing agent comprises a monomeric polythiol. A monomeric polythiol refers to a compound having at least two terminal thiol groups. Examples of monomeric polythiols include dithiols of Formula (5).

Sulfur-Containing Michael Acceptor Adduct, Sulfur-Containing Polymer, and a Compound Having at Least Two Michael Acceptor Groups In certain embodiments, a composition comprises a sulfur-containing polymer having terminal groups reactive with Michael acceptors and a sulfur-containing Michael acceptor adduct. In certain embodiments, a composition comprises a sulfur-containing polymer having terminal groups reactive with Michael acceptors, a polyfunctional Michael acceptor, and a sulfur-containing Michael acceptor adduct.

In such compositions, a sulfur-containing polymer comprises at least two terminal groups reactive with Michael acceptor groups. In such compositions, the sulfur-containing polymer may be selected from a polythioether polymer, a polysulfide polymer, or a combination thereof, including a suitable polythioether polymer or polysulfide polymer provided by the present disclosure.

In certain embodiments, a sulfur-containing polymer is selected such that the terminal groups are reactive with the polyfunctional Michael acceptor and with the sulfur-containing Michael acceptor adduct. In certain embodiments, a sulfur-containing polymer comprises terminal thiol groups including any of the thiol-terminated polythioethers, thiol-terminated polysulfides, and combinations thereof, disclosed herein.

In certain embodiments of such compositions, a sulfur-containing Michael acceptor adduct comprises a polythioether Michael acceptor adduct provided by the present disclosure, a polysulfide Michael acceptor adduct provided by the present disclosure, or a combination thereof.

When a composition comprises a polyfunctional monomeric Michael acceptor, any suitable monomeric Michael acceptor having at least two Michael acceptor groups such as, for example, divinyl sulfone, a bis(vinylsulfonyl)alkanol, or other Michael acceptors and combinations thereof, including any of those disclosed herein may be used.

In certain embodiments, a sulfur-containing polymer is selected from a thiol-terminated polythioether of Formula (4), Formula (4a), and a combination thereof; a polyfunctional Michael acceptor adduct is selected from a polythioether Michael acceptor adduct of Formula (3), Formula (3a), and a combination thereof; and a polyfunctional monomeric Michael acceptor is selected from a compound having two or more activated alkenyl groups such as a vinyl ketone or a vinyl sulfone, such as divinyl sulfone or a bis(vinylsulfonyl)alkanol such as, for example, 1,3-bis(vinylsulfonyl)-2-propanol.

In such embodiments, the polyfunctional Michael acceptor and Michael acceptor adduct comprise 10 wt % to 90 wt % of the composition, from 20 wt % to 80 wt %, from 30 wt % to 70 wt %, and in certain embodiments, from 40 wt % to 60 wt %, where wt % is based on the total dry solids weight of the composition.

Compositions comprising a sulfur-containing polymer, a polyfunctional Michael acceptor, and a sulfur-containing polymer adduct may comprise a catalyst such as an amine catalyst including polyamine catalysts.

Examples of polyamines include, for example, aliphatic polyamines, cycloaliphatic polyamines, aromatic polyamines and mixtures thereof. In certain embodiments, the polyamine can include a polyamine having at least two functional groups independently chosen from primary amine (—NH₂), secondary amine (—NH—) and combinations thereof. In certain embodiments, the polyamine has at least two primary amine groups.

In certain embodiments, a polyamine is a sulfur-containing polyamine. Examples of suitable sulfur-containing polyamines are isomers of benzenediamine-bis(methylthio)-, such as 1,3-benzenediamine-4-methyl-2,6-bis(methylthio)- and 1,3-benzenediamine-2-methyl-4,6-bis(methylthio)-, having the structure:

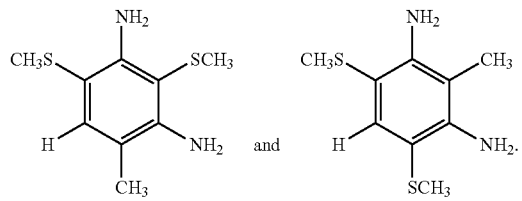

Such sulfur-containing polyamines are commercially available, for example, from Albemarle Corporation under the tradename Ethacure® 300. Can simple mention, because previously mentioned.

Suitable polyamines also include, for example, polyamines having the following structure:

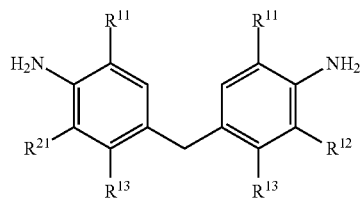

wherein each $R^{11}$ and each $R^{12}$ are independently selected from methyl, ethyl, propyl, and isopropyl groups, and each $R^{13}$ is independently selected from hydrogen and chlorine. Examples of suitable amine-containing curing agents include the following compounds available from Lonza Ltd. (Basel, Switzerland): Lonzacure® M-DIPA, Lonzacure® M-DMA, Lonzacure® M-MEA, Lonzacure® M-DEA, Lonzacure® M-MIPA, Lonzacure® M-CDEA.

In certain embodiments, a polyamine comprises a diamine, such as 4,4'-methylenebis(3-chloro-2,6-diethylaniline) (Lonzacure® M-CDEA), 2,4-diamino-3,5-diethyl-toluene, 2,6-diamino-3,5-diethyl-toluene and mixtures thereof (collectively diethyltoluenediamine or DETDA), a sulfur-containing diamine, such as Ethacure® 300, 4,4'-methylene-bis-(2-chloroaniline) and mixtures thereof. Other suitable diamines include 4,4'-methylene-bis(dialkylaniline), 4,4'-methylene-bis(2,6-dimethylaniline), 4,4'-methylene-bis(2,6-diethylaniline), 4,4'-methylene-bis(2-ethyl-6-methyla- niline), 4,4'-methylene-bis(2,6-diisopropylaniline), 4,4'-methylene-bis(2-isopropyl-6-methylaniline), 4,4'-methylene-bis(2,6-diethyl-3-chloroaniline), and combinations of any of the foregoing.

Further, examples of suitable polyamines include ethyleneamines, such as, ethylenediamine (EDA), diethylenetriamine (DETA), triethylenetetramine (TETA), tetraethylenepentamine (TEPA), pentaethylenehexamine (PEHA), piperazine, piperidine, substituted piperidine, diethylenediamine (DEDA), 2-amino-1-ethylpiperazine, and combinations thereof. In certain embodiments, a polyamine may be selected from one or more isomers of $C_{1-3}$ dialkyl toluenediamine, such as, 3,5-dimethyl-2,4-toluenediamine, 3,5-dimethyl-2,6-toluenediamine, 3,5-diethyl-2,4-toluenediamine, 3,5-diethyl-2,6-toluenediamine, 3,5-diisopropyl-2,4-toluenediamine, 3,5-diisopropyl-2,6-toluenediamine, and combinations thereof. In certain embodiments, a polyamine may be selected from methylene dianiline, trimethyleneglycol di(para-aminobenzoate), and combinations thereof.

In certain embodiments, a polyamine includes a compound having the structure:

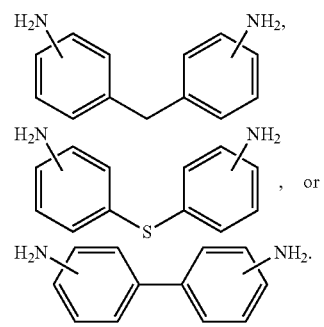

In certain embodiments, a polyamine includes one or more methylene bis anilines, one or more aniline sulfides, and/or one or more bianilines which can be represented by the general structures disclosed, for example, in paragraph [0072] of U.S. Publication No. 2011/0092639, which is incorporated by reference herein.

In certain embodiments, a polyamine includes compounds represented by the general structure:

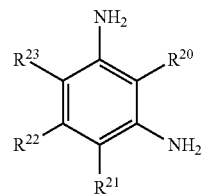

where $R^{20}$, $R^{21}$, $R^{22}$, and $R^{23}$ are independently selected from $C_{1-3}$ alkyl, $CH_3$—S— and halogen, such as but not limited to chlorine or bromine. In certain embodiments, a polyamine represented by the immediately preceding structure can be diethyl toluene diamine (DETDA) wherein $R^{23}$ is methyl, $R^{20}$ and $R^{21}$ are each ethyl, and $R^{22}$ is hydrogen. In certain embodiments, the polyamine is 4,4'-methylenedianiline.

Examples of blocked polyamines include ketimines, enamines, oxazolidines, aldimines, and imidazolidines. In certain embodiments, the blocked polyamine is Vestamin® A 139 (Evonik).

Epoxy Blend

In certain embodiments, compositions provided by the present disclosure comprise an epoxy curing agent. Thus, in addition to a Michael acceptor curing agent, a sulfur-containing polymer curing agent, and/or a sulfur-containing Michael acceptor adduct curing agent, a composition may comprise one or more polyepoxy curing agents. Examples of suitable epoxies include, for example, polyepoxide resins such as hydantoin diepoxide, diglycidyl ether of bisphenol-A, diglycidyl ether of bisphenol-F, Novolac® type epoxies such as DEN™ 438 (available from Dow), certain epoxidized unsaturated resins, and combinations of any of the foregoing. A polyepoxide refers to a compound having two or more reactive epoxy groups.

In certain embodiments, a polyepoxy curing agent comprises an epoxy-functional polymer. Examples of suitable epoxy-functional polymers include the epoxy-functional polyformal polymers disclosed in U.S. Publication 1 No. 2012/0238707 and epoxy-functional polythioether polymers disclosed in U.S. Pat. No. 7,671,145. In general, when used as a curing agent, an epoxy-functional polymer has a molecular weight less than about 2,000 Daltons, less than about 1,500, Daltons, less than about 1,000 Daltons, and in certain embodiments, less than about 500 Daltons. Epoxy-functional sulfur-containing polymers may be formed, for example, by reacting a thiol-functional sulfur-containing polymer with a diepoxide or with an allyl ether.

In such compositions, an epoxy curing agent may comprise about 0.5 wt % to about 20 wt % of the composition, from about 1 wt % to about 10 wt %, from about 2 wt % to about 8 wt %, from about 2 wt % to about 6 wt %, and in certain embodiments, from about 3 wt % to about 5 wt %, where wt % is based on the total solids weight of the composition.

Isocyanate Blend

In certain embodiments, compositions provided by the present disclosure comprise an isocyanate curing agent. Thus, in addition to a Michael acceptor curing agent, a sulfur-containing polymer curing agent, and/or a sulfur-containing Michael acceptor adduct curing agent, a composition may comprise one or more polyisocyanate curing agents that are reactive with thiol groups but not reactive with Michael acceptor groups such as vinyl sulfone and bis(vinylsulfonyl) alkanol groups. Examples of suitable isocyanate curing agents include toluene diisocyanate, and combinations of any of the foregoing. Isocyanate curing agents are commercially available and include, for example, products under the tradenames Baydur® (Bayer MaterialScience), Desmodur® (Bayer MaterialScience), Solubond® (DSM), ECCO (ECCO), Vestanat® (Evonik), Irodur® (Huntsman), Rhodocoat™ (Perstorp), and Vanchem® (V.T. Vanderbilt). In certain embodiments, an isocyanate curing agent comprises an isocyanate-functional polymer. Examples of suitable isocyanate-functional polymers include the isocyanate-functional polyformal polymers disclosed in U.S. Publication No. 2012/0238708. In general, when used as a curing agent, an isocyanate-functional polymer has a molecular weight less than about 2,000 Daltons, less than about 1,500, Daltons, less than about 1,000 Daltons, and in certain embodiments, less than about 500 Daltons.

In such compositions, an isocyanate curing agent may comprise about 0.5 wt % to about 20 wt % of the composition, from about 1 wt % to about 10 wt %, from about 2 wt % to about 8 wt %, from about 2 wt % to about 6 wt %, and in certain embodiments, from about 3 wt % to about 5 wt % of the composition, where wt % is based on the total solids weight of the composition.

Hydroxyl and Amine Curing

Sulfur-containing Michael acceptor adducts provided by the present disclosure may also be modified for use in particular applications and curing chemistries. For example, spray seal applications require rapid curing without heating. Amine-based systems using epoxy curing agents are well suited for such applications. Accordingly, sulfur-containing Michael acceptor adducts may be adapted to other curing chemistries by modifying or capping the terminal Michael acceptor groups with, for example, hydroxyl groups or amine groups.

Hydroxyl-terminated sulfur-containing Michael acceptor adducts may be prepared by reacting a sulfur-containing Michael acceptor adduct provided by the present disclosure such as an adduct of Formula (3) or Formula (3a) with a compound having a terminal thiol group and a terminal hydroxyl group. In certain embodiments, a compound having a terminal thiol group and a terminal hydroxyl group has the structure HS—$R^{11}$—OH, where $R^{11}$ is selected from $C_{2-6}$ alkanediyl, $C_{6-8}$ cycloalkanediyl, $C_{6-10}$ alkanecycloalkanediyl, $C_{5-8}$ heterocycloalkanediyl, $C_{6-8}$ arenediyl, $C_{6-10}$ alkanearenediyl, $C_{5-8}$ heteroarenediyl, and -[(—$CHR^3$-)$_s$—X-]$_q$—($CHR^3$)$_r$—, where q, r, s, X, and $R^3$ are defined as for Formula (5). In certain embodiments, a sulfur-containing Michael acceptor adduct is derived from Permapol® 3.1E. The reaction may take place in the presence of a catalyst at a temperature from about 25° C. to about 50° C.

In certain embodiments, a hydroxyl-terminated sulfur-containing Michael acceptor adduct comprises a hydroxyl-terminated polythioether Michael acceptor adduct of Formula (8), a hydroxyl-terminated polythioether adduct of Formula (8a), or a combination thereof:

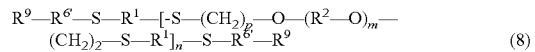

(8)

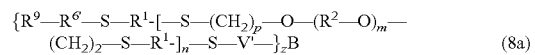

(8a)

wherein:
each $R^1$ independently is selected from $C_{2-10}$ alkanediyl, $C_{6-8}$ cycloalkanediyl, $C_{6-10}$ alkanecycloalkanediyl, $C_{5-8}$ heterocycloalkanediyl, and -[(—$CHR^3$-)$_s$—X-]$_q$-(—$CHR^3$-)$_r$—, wherein:
  s is an integer from 2 to 6;
  q is an integer from 1 to 5;
  r is an integer from 2 to 10;
  each $R^3$ is independently selected from hydrogen and methyl; and
  each X is independently selected from —O—, —S—, and —NR, wherein R is selected from hydrogen and methyl;
each $R^2$ is independently selected from $C_{1-10}$ alkanediyl, $C_{6-8}$ cycloalkanediyl, $C_{6-14}$ alkanecycloalkanediyl, and -[(—$CHR^3$-)$_s$—X-]$_q$-(—$CHR^3$-)$_r$—, wherein s, q, r, $R^3$, and X are as defined for $R^1$;
m is an integer from 0 to 50;
n is an integer from 1 to 60;
p is an integer from 2 to 6;
B represents a core of a z-valent, vinyl-terminated polyfunctionalizing agent B(—V)$_z$, wherein:
  z is an integer from 3 to 6; and
  each V is a group comprising a terminal group reactive with thiol groups;

each —V'— is derived from the reaction of —V with a thiol;

each —R⁶'— is a group derived from a compound having a terminal Michael acceptor group and a group reactive with a thiol group; and each R⁹— is a moiety having a terminal hydroxyl group.

In certain embodiments of Formula (8) and Formula (8a), each R⁹ is —S—R¹¹—OH, wherein R¹¹ is defined herein.

In certain embodiments of hydroxyl-terminated sulfur-containing Michael acceptor adducts of Formula (8) and Formula (8a), each R⁶' is derived from a vinyl sulfone, such as divinyl sulfone or from a bis(sulfonyl)alkanol such as a bis(vinylsulfonyl)alkanol such as 1,3-bis(vinylsulfonyl)-2-propanol. Thus, in certain embodiments, R⁶' has the structure —CH₂—C(R⁴)₂—S(O)₂—C(R⁴)₂—CH₂—, wherein each R⁴ is independently selected from hydrogen and C₁₋₃ alkyl; or —CH₂—CH₂—S(O)₂—R¹⁵—CH(—OH)—R¹⁵—S(O)₂—CH₂—CH₂— wherein each R¹⁵ is independently selected from C₁₋₃ alkanediyl and substituted C₁₋₃ alkanediyl, where the one or more substituent groups is —OH, such as, for example, —CH₂—CH₂—S(O)₂—CH₂—CH(—OH)—CH₂—S(O)₂—CH₂—CH₂—.

In certain embodiments, compositions comprise one or more hydroxyl-terminated sulfur-containing Michael acceptor adducts and one or more polyisocyanate curing agents. Examples of suitable isocyanate curing agents include toluene diisocyanate, and combinations of any of the foregoing. Isocyanate curing agents are commercially available and include, for example, products under the tradenames Baydur® (Bayer MaterialScience), Desmodur® (Bayer MaterialScience), Solubond® (DSM), ECCO (ECCO), Vestanat® (Evonik), Irodur® (Huntsman), Rhodocoat™ (Perstorp), and Vanchem® (V.T. Vanderbilt).

Amine-terminated sulfur-containing Michael acceptor adducts may be prepared by reacting a sulfur-containing Michael acceptor adduct provided by the present disclosure such as an adduct of Formula (3) or Formula (3a) with a compound having a terminal thiol group and a terminal amine group. In certain embodiments, a compound having a terminal thiol group and a terminal amine group has the structure HS—R¹¹—N(R¹²)H, where R¹¹ is selected from C₂₋₆ alkanediyl, C₆₋₈ cycloalkanediyl, C₆₋₁₀ alkanecycloalkanediyl, C₅₋₈ heterocycloalkanediyl, C₆₋₈ arenediyl, C₆₋₁₀ alkanearenediyl, C₅₋₈ heteroarenediyl, and -[—(CHR³)ₛ—X-]_q—(CHR³)ᵣ—, where q, r, s, X, and R³ are defined as for Formula (5). In certain embodiments, R¹² is selected from hydrogen and C₁₋₃ alkyl, and in certain embodiments, R¹² is hydrogen. In certain embodiments, an amine-terminated sulfur-containing Michael acceptor adduct is derived from Permapol® 3.1E. The reaction may take place in the presence of a catalyst at a temperature from about 25° C. to about 50° C.

In certain embodiments, an amine-terminated sulfur-containing Michael acceptor adduct comprises an amine-terminated polythioether adduct of Formula (8), an amine-terminated polythioether adduct of Formula (8a), or a combination thereof:

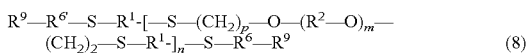

(8)

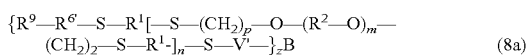

(8a)

wherein:

each R¹ independently is selected from C₂₋₁₀ alkanediyl, C₆₋₈ cycloalkanediyl, C₆₋₁₀ alkanecycloalkanediyl, C₅₋₈ heterocycloalkanediyl, and -[—(CHR³)ₛ—X-]_q—(CHR³)ᵣ—, wherein:

s is an integer from 2 to 6;

q is an integer from 1 to 5;

r is an integer from 2 to 10;

each R³ is independently selected from hydrogen and methyl; and each X is independently selected from —O—, —S—, and —NR, wherein R is selected from hydrogen and methyl;

each R² is independently selected from C₁₋₁₀ alkanediyl, C₆₋₈ cycloalkanediyl, C₆₋₁₄ alkanecycloalkanediyl, and -[—(CHR³)ₛ—X-]_q—(CHR³)ᵣ—, wherein s, q, r, R³, and X are as defined for R¹;

m is an integer from 0 to 50;

n is an integer from 1 to 60;

p is an integer from 2 to 6;

B represents a core of a z-valent, vinyl-terminated polyfunctionalizing agent B(—V)_z, wherein:

z is an integer from 3 to 6; and each V is a group comprising a terminal group reactive with thiol groups;

each —V' is derived from the reaction of V with a thiol;

each —R⁶'— is a group derived from a compound having a terminal Michael acceptor group and a group reactive with a thiol group; and each R⁹— is a moiety having a terminal amine group.

In certain embodiments, R⁹ is —S—R¹¹—N(R¹²)H, and in certain embodiments of Formula (8) and Formula (8a), R⁹ is —S—R¹¹—NH₂.

In certain embodiments of amine-terminated sulfur-containing Michael acceptor adducts of Formula (8) and Formula (8a), each R⁶' is derived from a vinyl sulfone, such as divinyl sulfone or from a bis(sulfonyl)alkanol such as a bis(vinylsulfonyl)alkanol such as 1,3-bis(vinylsulfonyl)-2-propanol. Thus, in certain embodiments, R⁶' has the structure —CH₂—C(R⁴)₂—S(O)₂—C(R⁴)₂—CH₂—, wherein each R⁴ is independently selected from hydrogen and C₁₋₃ alkyl; or —CH₂—CH₂—S(O)₂—R¹⁵—CH(—OH)—R¹⁵—S(O)₂—CH₂—CH₂— wherein each R¹⁵ is independently selected from C₁₋₃ alkanediyl and substituted C₁₋₃ alkanediyl, where the one or more substituent groups is OH, such as, for example, —CH₂—CH₂—S(O)₂—CH₂—CH(—OH)—CH₂—S(O)₂—CH₂—CH₂—. In certain embodiments, compositions comprise one or more amine-terminated sulfur-containing Michael acceptor adducts and one or more polyisocyanate curing agents such as any of those disclosed herein.

Additional Components

Compositions provided by the present disclosure may include one or more catalysts. Catalysts appropriate for use in reactions between Michael acceptors such as activated alkenyl groups and thiol groups include base catalysts such as amines. Examples of suitable amine catalysts include, for example, triethylenediamine(1,4-diazabicyclo[2.2.2]octane, DABCO), dimethylcyclohexylamine (DMCHA), dimethylethanolamine (DMEA), bis-(2-dimethylaminoethyl)ether, N-ethylmorpholine, triethylamine, 1,8-diazabicyclo[5.4.0]undecene-7 (DBU), pentamethyldiethylenetriamine (PMDETA), benzyldimethylamine (BDMA), N,N,N'-trimethyl-N'-hydroxyethyl-bis(aminoethyl)ether, and N'-(3-(dimethylamino)propyl)-N,N-dimethyl-1,3-propanediamine.

In compositions comprising epoxies, the composition may comprise a base catalyst, including amine catalysts such as any of those disclosed herein.

In certain embodiments, compositions provided by the present disclosure comprise one or more adhesion promoters. An adhesion promoter may be present in amount from 0.1 wt % to 15 wt % of a composition, less than 5 wt %, less than 2 wt %, and in certain embodiments, less than 1 wt %, based on the total dry weight of the composition. Examples of adhesion promoters include phenolics, such as Methylon® phenolic resin, and organosilanes, such as epoxy, mercapto or amino functional silanes, such as Silquest® A-187 and Silquest® A-1100. Other useful adhesion promoters are known in the art.

Compositions provided by the present disclosure may comprise one or more different types of filler. Suitable fillers include those commonly known in the art, including inorganic fillers, such as carbon black and calcium carbonate ($CaCO_3$), silica, polymer powders, and lightweight fillers. Suitable lightweight fillers include, for example, those described in U.S. Pat. No. 6,525,168. In certain embodiments, a composition includes 5 wt % to 60 wt % of the filler or combination of fillers, 10 wt % to 50 wt %, and in certain embodiments, from 20 wt % to 40 wt %, based on the total dry weight of the composition. Compositions provided by the present disclosure may further include one or more colorants, thixotropic agents, accelerators, fire retardants, adhesion promoters, solvents, masking agents, or a combination of any of the foregoing. As can be appreciated, fillers and additives employed in a composition may be selected so as to be compatible with each other as well as the polymeric component, curing agent, and or catalyst.

In certain embodiments, compositions provided by the present disclosure comprise at least one filler that is effective in reducing the specific gravity of the composition. In certain embodiments, the specific gravity of a composition is from 0.8 to 1, 0.7 to 0.9, from 0.75 to 0.85, and in certain embodiments, is 0.8. In certain embodiments, the specific gravity of a composition is less than about 0.9, less than about 0.8, less than about 0.75, less than about 0.7, less than about 0.65, less than about 0.6, and in certain embodiments, less than about 0.55.

In certain embodiments, compositions provided by the present disclosure include low density filler particles. As used herein, low density, when used with reference to such particles means that the particles have a specific gravity of no more than 0.7, in certain embodiments no more than 0.25, and in certain embodiments, no more than 0.1. Suitable lightweight filler particles often fall within two categories—microspheres and amorphous particles. The specific gravity of microspheres may range from 0.1 to 0.7 and include, for example, polystyrene foam, microspheres of polyacrylates and polyolefins, and silica microspheres having particle sizes ranging from 5 to 100 microns and a specific gravity of 0.25 (Eccospheres®). Other examples include alumina/silica microspheres having particle sizes in the range of 5 to 300 microns and a specific gravity of 0.7 (Fillite®), aluminum silicate microspheres having a specific gravity of from about 0.45 to about 0.7 (Z-Light®), calcium carbonate-coated polyvinylidene copolymer microspheres having a specific gravity of 0.13 (Dualite® 6001AE), and calcium carbonate coated acrylonitrile copolymer microspheres such as Dualite® E135, having an average particle size of about 40 µm and a density of 0.135 g/cc (Henkel). Suitable fillers for decreasing the specific gravity of the composition include, for example, hollow microspheres such as Expancel® microspheres (available from AkzoNobel) or Dualite® low density polymer microspheres (available from Henkel). In certain embodiments, compositions provided by the present disclosure include lightweight filler particles comprising an exterior surface coated with a thin coating, such as those described in U.S. Publication No. 2010/0041839 at paragraphs [0016]-[0052], the cited portion of which is incorporated by reference.

In certain embodiments, a low density filler comprises less than 2 wt % of a composition, less than 1.5 wt %, less than 1.0 wt %, less than 0.8 wt %, less than 0.75 wt % less than 0.7 wt % and in certain embodiments, less than 0.5 wt % of a composition, where wt % is based on the total dry solids weight of the composition.

In certain embodiments, compositions provided by the present disclosure comprise an electrically conductive filler. Electrical conductivity and EMI/RFI shielding effectiveness can be imparted to composition by incorporating conductive materials within the polymer. The conductive elements can include, for example, metal or metal-plated particles, fabrics, meshes, fibers, and combinations thereof. The metal can be in the form of, for example, filaments, particles, flakes, or spheres. Examples of metals include copper, nickel, silver, aluminum, tin, and steel. Other conductive materials that can be used to impart EMI/RFI shielding effectiveness to polymer compositions include conductive particles or fibers comprising carbon or graphite. Conductive polymers such as polythiophenes, polypyrroles, polyaniline, poly(p-phenylene) vinylene, polyphenylene sulfide, polyphenylene, and polyacetylene can also be used.

Electrically conductive fillers also include high band gap materials such as zinc sulfide and inorganic barium compounds.

Other examples of electrically conductive fillers include electrically conductive noble metal-based fillers such as pure silver; noble metal-plated noble metals such as silver-plated gold; noble metal-plated non-noble metals such as silver plated cooper, nickel or aluminum, for example, silver-plated aluminum core particles or platinum-plated copper particles; noble-metal plated glass, plastic or ceramics such as silver-plated glass microspheres, noble-metal plated aluminum or noble-metal plated plastic microspheres; noble-metal plated mica; and other such noble-metal conductive fillers. Non-noble metal-based materials can also be used and include, for example, non-noble metal-plated non-noble metals such as copper-coated iron particles or nickel plated copper; non-noble metals, e.g., copper, aluminum, nickel, cobalt; non-noble-metal-plated-non-metals, e.g., nickel-plated graphite and non-metal materials such as carbon black and graphite. Combinations of electrically conductive fillers can also be used to meet the desired conductivity, EMI/RFI shielding effectiveness, hardness, and other properties suitable for a particular application.

The shape and size of the electrically conductive fillers used in the compositions of the present disclosure can be any appropriate shape and size to impart electrical conductivity and/or EMI/RFI shielding effectiveness to the cured composition. For example, fillers can be of any shape that is generally used in the manufacture of electrically conductive fillers, including spherical, flake, platelet, particle, powder, irregular, fiber, and the like. In certain sealant compositions of the disclosure, a base composition can comprise Ni-coated graphite as a particle, powder or flake. In certain embodiments, the amount of Ni-coated graphite in a base composition can range from 40 wt % to 80 wt %, and in certain embodiments can range from 50 wt % to 70 wt %, based on the total weight of the base composition. In certain embodiments, an electrically conductive filler can comprise Ni fiber. Ni fiber can have a diameter ranging from 10 µm to 50 µm and have a length ranging from 250 µm to 750 µm. A base composition can comprise, for example, an amount of Ni fiber ranging from 2 wt % to 10 wt %, and in certain embodiments, from 4 wt % to 8 wt %, based on the total weight of the base composition.

Carbon fibers, particularly graphitized carbon fibers, can also be used to impart electrical conductivity to compositions of the present disclosure. Carbon fibers formed by vapor phase pyrolysis methods and graphitized by heat treatment and which are hollow or solid with a fiber diameter ranging from 0.1 micron to several microns, have high electrical conductivity. As disclosed in U.S. Pat. No. 6,184,280, carbon microfibers, nanotubes or carbon fibrils having an outer diameter of less than 0.1 µm to tens of nanometers can be used as electrically conductive fillers. An example of graphitized carbon fiber suitable for conductive compositions of the present disclosure include Panex® 3OMF (Zoltek Companies, Inc., St. Louis, Mo.), a 0.921 µm diameter round fiber having an electrical resistivity of $0.00055\Omega$-cm.

The average particle size of an electrically conductive filler can be within a range useful for imparting electrical conductivity to a polymer-based composition. For example, in certain embodiments, the particle size of the one or more fillers can range from 0.25 µm to 250 µm, in certain embodiments can range from 0.25 µm to 75 µm, and in certain embodiments can range from 0.25 µm to 60 µm. In certain embodiments, composition of the present disclosure can comprise Ketjen Black EC-600 JD (Akzo Nobel, Inc., Chicago, Ill.), an electrically conductive carbon black characterized by an iodine absorption of 1000-11500 mg/g (J0/84-5 test method), and a pore volume of 480-510 $cm^3/100$ gm (DBP absorption, KTM 81-3504). In certain embodiments, an electrically conductive carbon black filler is Black Pearls 2000 (Cabot Corporation, Boston, Mass.).

In certain embodiments, electrically conductive polymers can be used to impart or modify the electrical conductivity of compositions of the present disclosure. Polymers having sulfur atoms incorporated into aromatic groups or adjacent to double bonds, such as in polyphenylene sulfide, and polythiophene, are known to be electrically conductive. Other electrically conductive polymers include, for example, polypyrroles, polyaniline, poly(p-phenylene) vinylene, and polyacetylene. In certain embodiments, the sulfur-containing polymers forming a base composition can be polysulfides and/or polythioethers. As such, the sulfur-containing polymers can comprise aromatic sulfur groups and sulfur atoms adjacent to conjugated double bonds to enhance the electrical conductivity of the compositions of the present disclosure.

Compositions of the present disclosure can comprise more than one electrically conductive filler and the more than one electrically conductive filler can be of the same or different materials and/or shapes. For example, a sealant composition can comprise electrically conductive Ni fibers, and electrically conductive Ni-coated graphite in the form of powder, particles or flakes. The amount and type of electrically conductive filler can be selected to produce a sealant composition which, when cured, exhibits a sheet resistance (four-point resistance) of less than $0.50\Omega \cdot /cm^2$, and in certain embodiments, a sheet resistance less than $0.15\Omega/cm^2$. The amount and type of filler can also be selected to provide effective EMI/RFI shielding over a frequency range of from 1 MHz to 18 GHz for an aperture sealed using a sealant composition of the present disclosure.

In certain embodiments, an electrically conductive base composition can comprise an amount of electrically non-conductive filler ranging from 2 wt % to 10 wt % based on the total weight of the base composition, and in certain embodiments, can range from 3 wt % to 7 wt %. In certain embodiments, a curing agent composition can comprise an amount of electrically non-conductive filler ranging from less than 6 wt % and in certain embodiments ranging from 0.5% to 4% by weight, based on the total weight of the curing agent composition.

Galvanic corrosion of dissimilar metal surfaces and the conductive compositions of the present disclosure can be minimized or prevented by adding corrosion inhibitors to the composition, and/or by selecting appropriate conductive fillers. In certain embodiments, corrosion inhibitors include strontium chromate, calcium chromate, magnesium chromate, and combinations thereof. U.S. Pat. No. 5,284,888 and U.S. Pat. No. 5,270,364 disclose the use of aromatic triazoles to inhibit corrosion of aluminum and steel surfaces. In certain embodiments, a sacrificial oxygen scavenger such as Zn can be used as a corrosion inhibitor. In certain embodiments, the corrosion inhibitor can comprise less than 10% by weight of the total weight of the electrically conductive composition. In certain embodiments, the corrosion inhibitor can comprise an amount ranging from 2% by weight to 8% by weight of the total weight of the electrically conductive composition. Corrosion between dissimilar metal surfaces can also be minimized or prevented by the selection of the type, amount, and properties of the conductive fillers comprising the composition.

In certain embodiments, a sulfur-containing polymer and/or sulfur-containing polymer Michael acceptor adduct comprises from about 50 wt % to about 90 wt % of a composition, from about 60 wt % to about 90 wt %, from about 70 wt % to about 90 wt %, and in certain embodiments, from about 80 wt % to about 90 wt % of the composition, where wt % is based on the total dry solids weight of the composition.

A composition may also include any number of additives as desired. Examples of suitable additives include plasticizers, pigments, surfactants, adhesion promoters, thixotropic agents, fire retardants, masking agents, and accelerators (such as amines, including 1,4-diazabicyclo[2.2.2]octane, DABCO®), and combinations of any of the foregoing. When used, the additives may be present in a composition in an amount ranging, for example, from about 0% to 60% by weight. In certain embodiments, additives may be present in a composition in an amount ranging from about 25% to 60% by weight.

Uses

Compositions provided by the present disclosure may be used, for example, in sealants, coatings, encapsulants, and potting compositions. A sealant includes a composition capable of producing a film that has the ability to resist operational conditions, such as moisture and temperature, and at least partially block the transmission of materials, such as water, fuel, and other liquid and gases. A coating composition includes a covering that is applied to the surface of a substrate to, for example, improve the properties of the substrate such as the appearance, adhesion, wettability, corrosion resistance, wear resistance, fuel resistance, and/or abrasion resistance. A potting composition includes a material useful in an electronic assembly to provide resistance to shock and vibration and to exclude moisture and corrosive agents. In certain embodiments, sealant compositions provided by the present disclosure are useful, e.g., as aerospace sealants and as linings for fuel tanks.

In certain embodiments, compositions, such as sealants, may be provided as multi-pack compositions, such as two-pack compositions, wherein one package comprises one or more thiol-terminated polythioethers provided by the present disclosure and a second package comprises one or more polyfunctional sulfur-containing epoxies provided by the present disclosure. Additives and/or other materials may be added to either package as desired or necessary. The two packages may be combined and mixed prior to use. In certain embodiments, the pot life of the one or more mixed thiol-terminated polythioethers and epoxies is at least 30 minutes, at least 1 hour, at least 2 hours, and in certain embodiments, more than 2 hours, where pot life refers to the period of time the mixed composition remains suitable for use as a sealant after mixing.

Compositions, including sealants, provided by the present disclosure may be applied to any of a variety of substrates. Examples of substrates to which a composition may be applied include metals such as titanium, stainless steel, and aluminum, any of which may be anodized, primed, organic-coated or chromate-coated; epoxy; urethane; graphite; fiberglass composite; Kevlar®; acrylics; and polycarbonates. In certain embodiments, compositions provided by the present disclosure may be applied to a coating on a substrate, such as a polyurethane coating.

Compositions provided by the present disclosure may be applied directly onto the surface of a substrate or over an underlayer by any suitable coating process known to those of ordinary skill in the art.

Furthermore, methods are provided for sealing an aperture utilizing a composition provided by the present disclosure. These methods comprise, for example, applying a composition provided by the present disclosure to a surface to seal an aperture, and curing the composition. In certain embodiments, a method for sealing an aperture comprises (a) applying a sealant composition provided by the present disclosure to one or more surfaces defining an aperture, (b) assembling the surfaces defining the aperture, and (c) curing the sealant, to provide a sealed aperture.

In certain embodiments, a composition may be cured under ambient conditions, where ambient conditions refers to a temperature from 20° C. to 25° C., and atmospheric humidity. In certain embodiments, a composition may be cured under conditions encompassing a temperature from a 0° C. to 100° C. and humidity from 0% relative humidity to 100% relative humidity. In certain embodiments, a composition may be cured at a higher temperature such as at least 30° C., at least 40° C., and in certain embodiments, at least 50° C. In certain embodiments, a composition may be cured at room temperature, e.g., 25° C. In certain embodiments, a composition may be cured upon exposure to actinic radiation, such as ultraviolet radiation. As will also be appreciated, the methods may be used to seal apertures on aerospace vehicles including aircraft and aerospace vehicles.

In certain embodiments, the composition achieves a tack-free cure in less than about 2 hours, less than about 4 hours, less than about 6 hours, less than about 8 hours, and in certain embodiments, less than about 10 hours, at a temperature of less than about 200° F.

The time to form a viable seal using curable compositions of the present disclosure can depend on several factors as can be appreciated by those skilled in the art, and as defined by the requirements of applicable standards and specifications. In general, curable compositions of the present disclosure develop adhesion strength within 24 hours to 30 hours, and 90% of full adhesion strength develops from 2 days to 3 days, following mixing and application to a surface. In general, full adhesion strength as well as other properties of cured compositions of the present disclosure becomes fully developed within 7 days following mixing and application of a curable composition to a surface.

Cured compositions disclosed herein, such as cured sealants, exhibit properties acceptable for use in aerospace applications. In general, it is desirable that sealants used in aviation and aerospace applications exhibit the following properties: peel strength greater than 20 pounds per linear inch (pli) on Aerospace Material Specification (AMS) 3265B substrates determined under dry conditions, following immersion in JRF Type I for 7 days, and following immersion in a solution of 3% NaCl according to AMS 3265B test specifications; tensile strength between 300 pounds per square inch (psi) and 400 psi; tear strength greater than 50 pounds per linear inch (pli); elongation between 250% and 300%; and hardness greater than 40 Durometer A. These and other cured sealant properties appropriate for aviation and aerospace applications are disclosed in AMS 3265B, the entirety of which is incorporated herein by reference. It is also desirable that, when cured, compositions of the present disclosure used in aviation and aircraft applications exhibit a percent volume swell not greater than 25% following immersion for one week at 60° C. (140° F.) and ambient pressure in JRF Type I. Other properties, ranges, and/or thresholds may be appropriate for other sealant applications.

In certain embodiments, therefore, compositions provided by the present disclosure are fuel-resistant. As used herein, the term "fuel resistant" means that a composition, when applied to a substrate and cured, can provide a cured product, such as a sealant, that exhibits a percent volume swell of not greater than 40%, in some cases not greater than 25%, in some cases not greater than 20%, in yet other cases not more than 10%, after immersion for one week at 140° F. (60° C.) and ambient pressure in Jet Reference Fluid (JRF) Type I according to methods similar to those described in ASTM D792 (American Society for Testing and Materials) or AMS 3269 (Aerospace Material Specification). Jet Reference Fluid JRF Type I, as employed for determination of fuel resistance, has the following composition: toluene: 28%±1% by volume; cyclohexane (technical): 34%±1% by volume; isooctane: 38%±1% by volume; and tertiary dibutyl disulfide: 1%±0.005% by volume (see AMS 2629, issued Jul. 1, 1989, §3.1.1 etc., available from SAE (Society of Automotive Engineers)).

In certain embodiments, compositions provided herein provide a cured product, such as a sealant, exhibiting a tensile elongation of at least 100% and a tensile strength of at least 400 psi when measured in accordance with the procedure described in AMS 3279, §3.3.17.1, test procedure AS5127/1, §7.7.

In certain embodiments, compositions provide a cured product, such as a sealant, that exhibits a lap shear strength of greater than 200 psi, such as at least 220 psi, at least 250 psi, and, in some cases, at least 400 psi, when measured according to the procedure described in SAE AS5127/1 paragraph 7.8.

In certain embodiments, a cured sealant comprising a composition provided by the present disclosure meets or exceeds the requirements for aerospace sealants as set forth in AMS 3277.

Apertures, including apertures of aerospace vehicles, sealed with compositions provided by the present disclosure are also disclosed.

In certain embodiments, a cured sealant provided by the present disclosure exhibits the following properties when cured for 2 days at room temperature, 1 day at 140° F., and 1 day at 200° F.: a dry hardness of 49, a tensile strength of 428 psi, and an elongation of 266%; and after 7 days in JRF Type I, a hardness of 36, a tensile strength of 312 psi, and an elongation of 247%.

In certain embodiments, compositions provided by the present disclosure exhibit a Shore A hardness (following 7-day cure) greater than 10, greater than 20, greater than 30, and in certain embodiments, greater than 40; a tensile strength greater than 10 psi, greater than 100 psi, greater than 200 psi, and in certain embodiments, greater than 500 psi; an elongation greater than 100%, greater than 200%, greater than 500%, and in certain embodiments, greater than 1,000%; and a swell following exposure to JRF Type I (7 days) less than 20%.

Cured sealants prepared from bis(sulfonyl)alkanol-containing sulfur-containing polymers provided by the present disclosure exhibit enhanced tensile strength and enhanced adhesion to metal surfaces. Bis(sulfonyl)alkanols can serve as polydentate ligands in metal chelates. It is believed that similar chelation occurs with exposed metals such as aluminum that enhances the bonding of the bis(sulfonyl)alkanol-containing sulfur-containing polymers to metal surfaces.

EXAMPLES

Embodiments provided by the present disclosure are further illustrated by reference to the following examples, which describe the synthesis, properties, and uses of certain sulfur-containing polymers, Michael acceptor adducts, and compositions comprising sulfur-containing polymers, Michael acceptor adducts, and Michael acceptors. It will be apparent to those skilled in the art that many modifications, both to materials, and methods, may be practiced without departing from the scope of the disclosure.

Example 1

Synthesis of Thiol-Terminated Polythioether Polymer

In a 50-gallon reactor, 128 lbs of diethylene glycol divinyl ether (DEG-DVE) and 173 lbs of dimercaptodioxaoctane (DMDO) were mixed with 6 lbs of triallylcyanurate (TAC) and heated to 77° C. To the heated reaction mixture was added 0.2 lb of an azobisnitrile free radical catalyst (Vazo™ 67,2, 2'-azobis(2-methylbutyronitrile), DuPont). The reaction proceeded substantially to completion after 24 hours to afford a liquid thiol-terminated resin having a mercaptan equivalent weight of 1,522.

Example 2

Synthesis of Bis(sulfonyl)alkanol-Terminated Polythioether Polymer

In a 2-liter flask, 319.6 g of the polymer of Example 1, 51.2 g of 1,3-bis(vinylsulfonyl)-2-propanol, 420 g of acetone, 63 g of toluene and 1.28 g of triethylamine were charged. The mixture was stirred for 16 hours at room temperature and the solvents were removed under vacuum. The product was a bis(sulfonyl)alkanol-terminated polythioether polymer.

Example 3

Sealant Composition

Twenty-nine and four-tenths (29.4) g of the polymer of Example 2, 22.8 g of the polymer of Example 1 and 26.1 g of calcium carbonate were placed in a 100-g plastic container. The contents were mixed in a high speed mixer for 60 seconds at 2,300 rpm. A portion of the mixed material was allowed to cure at room temperature for four days, followed by one day at 160° F. The hardness of the cured sealant was 52 Shore A.

A second portion of the mixed material was used to fabricate a tensile strength and elongation specimen. The specimen was cured at room temperature for four days, followed by one day at 160° F. Upon full cure, the tensile strength and elongation were measured according to ASTM D412. The specimen was further immersed in Jet Reference Fluid Type I for 7 days at 140° F. The tensile strength and elongation were measured again after the immersion. In addition, the volume swell and weight gain were measured according to SAE AS5127. The results of these measurements are shown in Table 1.

TABLE 1

| | Tensile Strength (psi) | Elongation (%) | Volume Swell (%) | Weight Gain (%) |
|---|---|---|---|---|
| Before Immersion | 897 | 795 | — | — |
| After Immersion | 403 | 775 | 15.5 | 2.31 |

Finally, it should be noted that there are alternative ways of implementing the embodiments disclosed herein. Accordingly, the present embodiments are to be considered as illustrative and not restrictive. Furthermore, the claims are not to be limited to the details given herein, and are entitled to their full scope and equivalents thereof.

What is claimed is:

1. A sulfur-containing Michael acceptor adduct comprising at least two terminal 1-(ethylenesulfonyl)-n-(vinylsulfonyl)alkanol groups.

2. The adduct of claim 1, wherein each of the at least two terminal 1-(ethylenesulfonyl)-n-(vinylsulfonyl)alkanol groups are 1-(ethylenesulfonyl)-3-(vinylsulfonyl)propan-2-ol groups.

3. The adduct of claim 1, wherein the adduct is selected from a polythioether Michael acceptor adduct of Formula (3), a polythioether Michael acceptor adduct of Formula (3a), and a combination thereof:

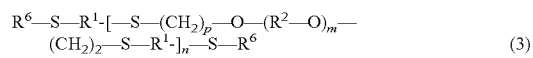

(3)

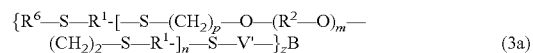

(3a)

wherein:
each $R^1$ independently is selected from $C_{2-10}$ alkanediyl, $C_{6-8}$ cycloalkanediyl, $C_{6-10}$ alkanecycloalkanediyl, $C_{5-8}$ heterocycloalkanediyl, and -[(—CHR$^3$-)$_s$—X-]$_q$-(—CHR$^3$-)$_r$—, wherein:
s is an integer from 2 to 6;
q is an integer from 1 to 5;
r is an integer from 2 to 10;
each $R^3$ is independently selected from hydrogen and methyl; and
each X is independently selected from —O—, —S—, and —NR—, wherein R is selected from hydrogen and methyl;
each $R^2$ is independently selected from $C_{1-10}$ alkanediyl, $C_{6-8}$ cycloalkanediyl, $C_{6-14}$ alkanecycloalkanediyl, and -[(—CHR$^3$-)$_s$—X-]$_q$-(—CHR$^3$-)$_r$—, wherein s, q, r, $R^3$, and X are as defined for $R^1$;
m is an integer from 0 to 50;
n is an integer from 1 to 60;
p is an integer from 2 to 6;

B represents a core of a z-valent, vinyl-terminated polyfunctionalizing agent B(—V)$_z$ wherein:
  z is an integer from 3 to 6; and
  each V is a group comprising a group reactive with thiol groups; and
  each —V'— is derived from the reaction of —V with a thiol; and
each R$^6$ is independently a moiety comprising a terminal 1-(ethylenesulfonyl)-n-(vinylsulfonyl)alkanol group.

4. The adduct of claim 3, wherein each R$^6$ has the structure of Formula (2):

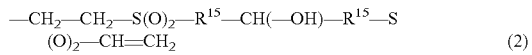

$$\text{—CH}_2\text{—CH}_2\text{—S(O)}_2\text{—R}^{15}\text{—CH(—OH)—R}^{15}\text{—S(O)}_2\text{—CH=CH}_2 \quad (2)$$

wherein each R$^{15}$ is independently selected from C$_{1-3}$ alkanediyl, and substituted C$_{1-3}$ alkanediyl, wherein the one or more substituent groups is —OH.

5. The adduct of claim 1, wherein the adduct comprises the reaction products of reactants comprising:
  (a) a sulfur-containing polymer; and
  (b) a compound having a terminal bis(sulfonyl)alkanol group and a group that is reactive with a terminal group of the sulfur-containing polymer.

6. The adduct of claim 5, wherein the sulfur-containing polymer comprises a thiol-terminated polythioether selected from a thiol-terminated polythioether polymer of Formula (4), a thiol-terminated polythioether polymer of Formula (4a), and a combination thereof:

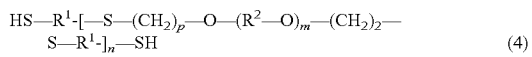

$$\text{HS—R}^1\text{-[—S—(CH}_2)_p\text{—O—(R}^2\text{—O)}_m\text{—(CH}_2)_2\text{—S—R}^1\text{-]}_n\text{—SH} \quad (4)$$

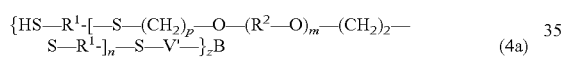

$$\{\text{HS—R}^1\text{-[—S—(CH}_2)_p\text{—O—(R}^2\text{—O)}_m\text{—(CH}_2)_2\text{—S—R}^1\text{-]}_n\text{—S—V'—}\}_z\text{B} \quad (4a)$$

wherein:
  each R$^1$ independently is selected from C$_{2-10}$ alkanediyl, C$_{6-8}$ cycloalkanediyl, C$_{6-14}$ alkanecycloalkanediyl, C$_{5-8}$ heterocycloalkanediyl, and -[(—CHR$^3$-)$_s$—X-]$_q$-(—CHR$^3$-)$_r$—, wherein:
    s is an integer from 2 to 6;
    q is an integer from 1 to 5;
    r is an integer from 2 to 10;
    each R$^3$ is independently selected from hydrogen and methyl; and
    each X is independently selected from —O—, —S—, and —NR—, wherein R is selected from hydrogen and methyl;
  each R$^2$ is independently selected from C$_{1-10}$ alkanediyl, C$_{6-8}$ cycloalkanediyl, C$_{6-14}$ alkanecycloalkanediyl, and -[(—CHR$^3$-)$_s$—X-]$_q$-(—CHR$^3$-)$_r$—, wherein s, q, r, R$^3$, and X are as defined for R$^1$;
  m is an integer from 0 to 50;
  n is an integer from 1 to 60;
  p is an integer from 2 to 6;
  B represents a core of a z-valent, vinyl-terminated polyfunctionalizing agent B(—V)$_z$ wherein:
    z is an integer from 3 to 6; and
    each —V is a group comprising a terminal group reactive with thiol groups; and
    each —V'— is derived from the reaction of —V with a thiol.

7. The adduct of claim 5, wherein the compound having a terminal bis(sulfonyl)alkanol group and a group that is reactive with a terminal group of the sulfur-containing polymer comprises 1,3-bis(vinylsulfonyl)-2-propanol.

8. A composition comprising:
  (a) a sulfur-containing polymer comprising at least two terminal groups reactive with Michael acceptor groups; and
  (b) a bis(vinylsulfonyl)alkanol.

9. The composition of claim 8, wherein the bis(vinylsulfonyl)alkanol is 1,3-bis(vinylsulfonyl)-2-propanol.

10. The composition of claim 8, comprising a polyepoxy.

11. The composition of claim 8, comprising a polysulfide polymer comprising at least two terminal groups reactive with Michael acceptor groups.

12. A composition comprising:
  (a) the sulfur-containing Michael acceptor adduct of claim 1; and
  (b) a curing agent comprising at least two terminal groups that are reactive with Michael acceptor groups.

13. The composition of claim 12, wherein the curing agent is selected from a sulfur-containing polymer comprising at least two terminal groups reactive with Michael acceptor groups, a monomeric thiol, a polythiol, a polyamine, a blocked amine, and a combination of any of the foregoing.

14. The composition of claim 12, wherein the curing agent comprises a sulfur-containing polymer comprising at least two terminal groups reactive with Michael acceptor groups.

15. The composition of claim 14, wherein the sulfur-containing polymer comprises a polythioether.

16. The composition of claim 15, wherein the polythioether comprises a thiol-terminated polythioether selected from a thiol-terminated polythioether polymer of Formula (4), a thiol-terminated polythioether polymer of Formula (4a), and a combination thereof:

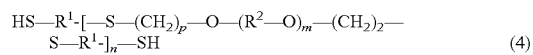

$$\text{HS—R}^1\text{-[—S—(CH}_2)_p\text{—O—(R}^2\text{—O)}_m\text{—(CH}_2)_2\text{—S—R}^1\text{-]}_n\text{—SH} \quad (4)$$

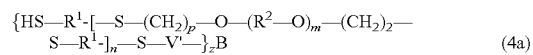

$$\{\text{HS—R}^1\text{-[—S—(CH}_2)_p\text{—O—(R}^2\text{—O)}_m\text{—(CH}_2)_2\text{—S—R}^1\text{-]}_n\text{—S—V'—}\}_z\text{B} \quad (4a)$$

wherein:
  each R$^1$ independently is selected from C$_{2-10}$ alkanediyl, C$_{6-8}$ cycloalkanediyl, C$_{6-14}$ alkanecycloalkanediyl, C$_{5-8}$ heterocycloalkanediyl, and -[(—CHR$^3$-)$_s$—X-]$_q$-(—CHR$^3$-)$_r$—, wherein:
    s is an integer from 2 to 6;
    q is an integer from 1 to 5;
    r is an integer from 2 to 10;
    each R$^3$ is independently selected from hydrogen and methyl; and
    each X is independently selected from —O—, —S—, and —NR—, wherein R is selected from hydrogen and methyl;
  each R$^2$ is independently selected from C$_{1-10}$ alkanediyl, C$_{6-8}$ cycloalkanediyl, C$_{6-14}$ alkanecycloalkanediyl, and -[(—CHR$^3$-)$_s$—X-]$_q$-(—CHR$^3$—)$_r$—, wherein s, q, r, R$^3$, and X are as defined as for R$^1$;
  m is an integer from 0 to 50;
  n is an integer from 1 to 60;
  p is an integer from 2 to 6;
  B represents a core of a z-valent, vinyl-terminated polyfunctionalizing agent B(—V)$_z$ wherein:
    z is an integer from 3 to 6; and
    each V is a group comprising a terminal group reactive with thiol groups; and
    each —V'— is derived from the reaction of —V with a thiol.

17. The composition of claim 14, wherein the sulfur-containing polymer comprises a polysulfide polymer.

18. The composition of claim 12, comprising a polyepoxy.

19. The composition of claim 12, comprising a polysulfide Michael acceptor adduct.

20. A composition comprising:
   (a) a sulfur-containing Michael acceptor adduct of claim 1;
   (b) a sulfur-containing polymer comprising at least two terminal groups reactive with Michael acceptor groups; and
   (c) a monomeric compound having at least two Michael acceptor groups.

21. The composition of claim 12, formulated as a sealant.

22. A cured sealant prepared using the composition of claim 21.

23. A method of sealing a surface comprising:
   providing a surface;
   applying the composition of claim 21 to the surface; and
   curing the composition to provide a sealed surface.

24. The composition of claim 20, formulated as a sealant.

25. A cured sealant prepared using the composition of claim 24.

26. A method of sealing a surface comprising:
   providing a surface;
   applying the composition of claim 24 to the surface; and
   curing the composition to provide a sealed surface.

* * * * *